US011389244B2

(12) United States Patent
Mulcahey et al.

(10) Patent No.: US 11,389,244 B2
(45) Date of Patent: Jul. 19, 2022

(54) DEVICES AND METHODS FOR ENERGY TRANSFER MAPPING

(71) Applicant: CSA Medical, Inc., Lexington, MA (US)

(72) Inventors: Thomas I. Mulcahey, Belmont, MA (US); Marc Davidson, Saco, ME (US)

(73) Assignee: CSA Medical, Inc., Lexington, MA (US)

( * ) Notice: Subject to any disclaimer, the term of this patent is extended or adjusted under 35 U.S.C. 154(b) by 416 days.

(21) Appl. No.: 16/523,658

(22) Filed: Jul. 26, 2019

(65) Prior Publication Data

US 2020/0030037 A1 Jan. 30, 2020

Related U.S. Application Data

(60) Provisional application No. 62/712,022, filed on Jul. 30, 2018.

(51) Int. Cl.
*A61B 34/10* (2016.01)
*H01R 13/66* (2006.01)
*G09B 23/30* (2006.01)
*A61B 17/00* (2006.01)
*A61B 18/02* (2006.01)
*A61B 18/18* (2006.01)
*A61B 18/00* (2006.01)

(52) U.S. Cl.
CPC .............. *A61B 34/10* (2016.02); *G09B 23/30* (2013.01); *H01R 13/6683* (2013.01); *A61B 18/18* (2013.01); *A61B 2017/00716* (2013.01); *A61B 2018/00779* (2013.01); *A61B 2018/0212* (2013.01); *A61B 2034/102* (2016.02); *A61B 2034/105* (2016.02); *H01R 2201/12* (2013.01)

(58) Field of Classification Search
CPC .............. A61B 34/10; A61B 2034/105; A61B 2034/107; H01L 35/34
See application file for complete search history.

(56) References Cited

U.S. PATENT DOCUMENTS 5,560,711 A * 10/1996 Bu .......................... G01W 1/17
257/467
5,909,004 A 6/1999 Hedengren et al.
(Continued)

OTHER PUBLICATIONS

International Search Report and Written Opinion for International Application No. PCT/US2019/043699, dated Nov. 11, 2019, 12 pages.
(Continued)

*Primary Examiner* — Kurt Fernstrom
(74) *Attorney, Agent, or Firm* — Goodwin Procter LLP

(57) ABSTRACT

The present disclosure relates generally to the field of energy transfer mapping, including fixtures with two-dimensional and three-dimensional sensor arrays. In particular, the present disclosure relates to devices and methods for mapping of energy transfer from and/or to an instrument inserted within and/or into body tissue, including the depths and patterns of penetration and/or amounts of energy transfer to and/or from an instrument delivered within biological tissue or materials that mimic biological tissue, including within fixtures with three-dimensional temperature sensor arrays configured to simulate anatomical geometries such as the gastrointestinal (GI) or respiratory tract.

17 Claims, 19 Drawing Sheets

(56) References Cited

U.S. PATENT DOCUMENTS

| | | | |
|---|---|---|---|
| 6,084,174 | A | 7/2000 | Hedengren et al. |
| 6,180,867 | B1 | 1/2001 | Hedengren et al. |
| 9,277,960 | B2 * | 3/2016 | Weinkam .................. A61B 5/01 |
| 11,129,670 | B2 * | 9/2021 | Shelton, IV ....... A61B 18/1445 |
| 2009/0221999 | A1 | 9/2009 | Shahidi |
| 2015/0025533 | A1 | 1/2015 | Groff et al. |
| 2015/0342671 | A1 | 12/2015 | Govari et al. |
| 2017/0027630 | A1 | 2/2017 | Wittenberger et al. |
| 2018/0078218 | A1 * | 3/2018 | Moisa .................... A61B 5/743 |
| 2019/0269367 | A1 * | 9/2019 | Reinders ................. A61B 5/01 |
| 2020/0003733 | A1 * | 1/2020 | Stanton ................ G01N 29/228 |
| 2020/0383837 | A1 * | 12/2020 | Gowans ................. A61B 5/445 |

OTHER PUBLICATIONS

Petti, L., et al, "Metal oxide semiconductor thin-film transistors for flexible electronics", Applied Physics Reviews 3(2):021303-1 through 021303-53 (2016).

Yang, Y.-J., et al., "An integrated flexible temperature and tactile sensing array using PI-copper films", Sensors and Actuators A; Physical, 143(1):1143-153 (2008).

\* cited by examiner

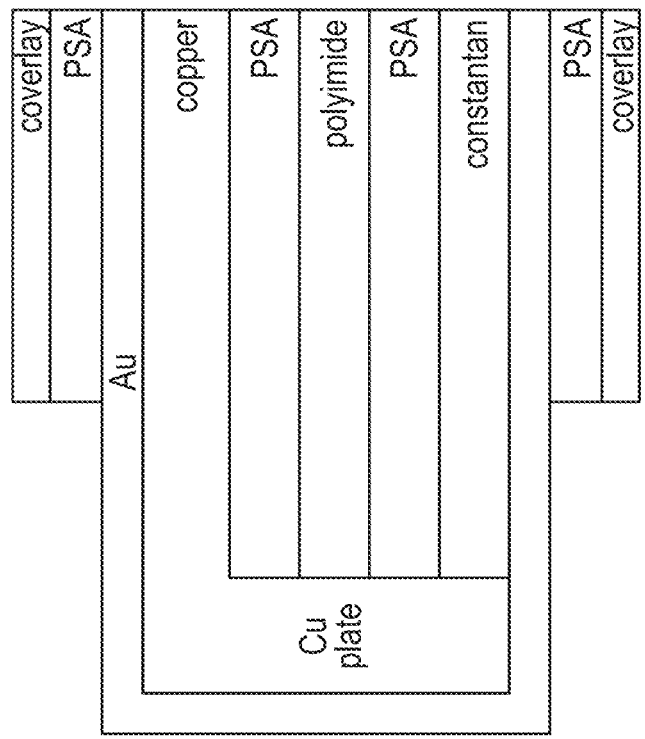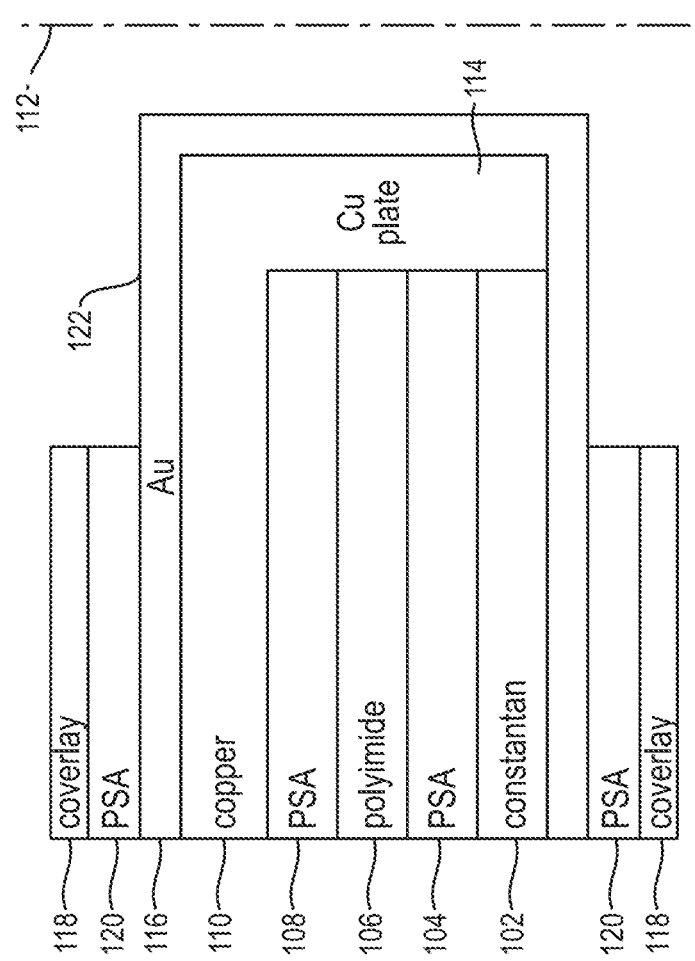
FIG. 1

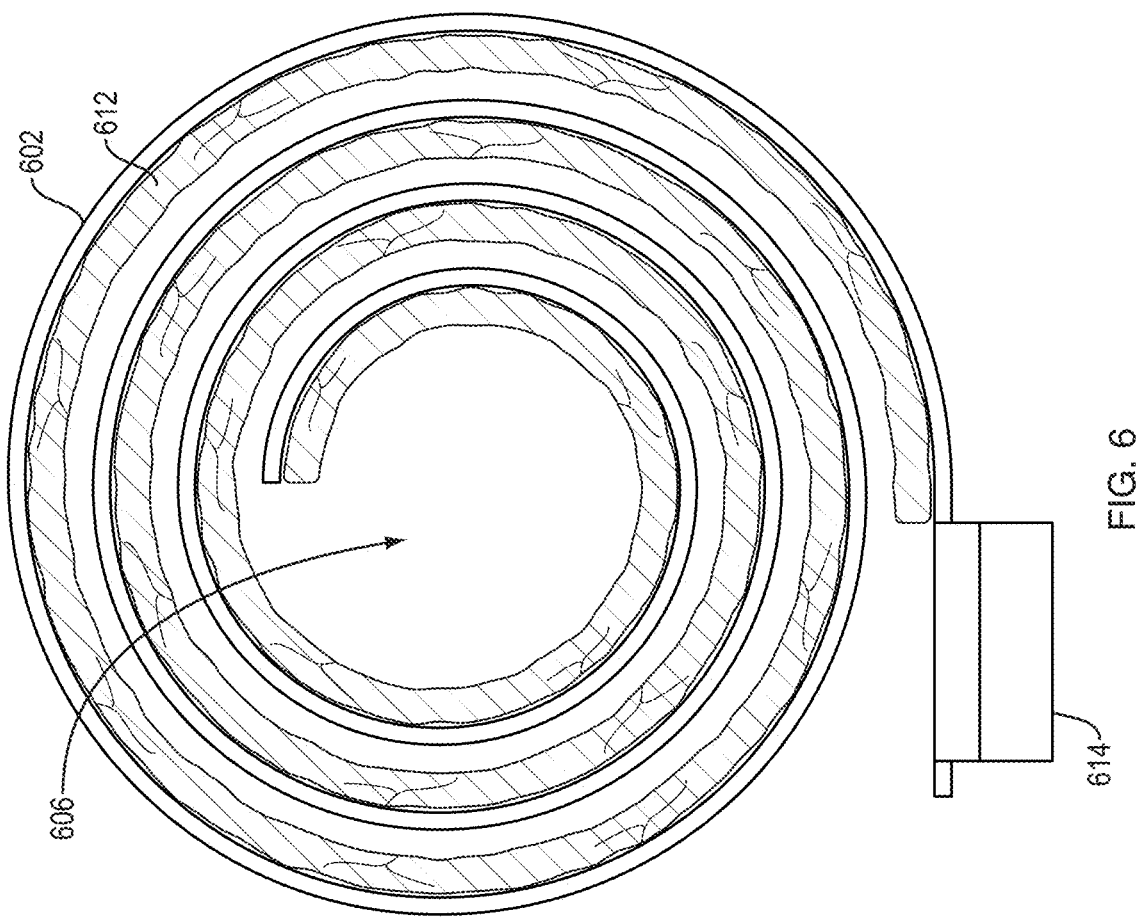

DEVICES AND METHODS FOR ENERGY TRANSFER MAPPING

PRIORITY

This application claims the benefit of priority under 35 USC § 119 to U.S. Provisional Patent Application Ser. No. 62/712,022, filed Jul. 30, 2018, which is incorporated by reference herein in its entirety and for all purposes.

FIELD

The present disclosure relates generally to the field of energy transfer mapping, including fixtures with two-dimensional and three-dimensional sensor arrays. In particular, the present disclosure relates to devices and methods for mapping of energy transfer from and/or to an instrument and/or body tissue, including the depths and patterns of penetration and/or amounts of energy transferred from/to an instrument inserted within or into biological tissue or materials that mimic biological tissue, including within fixtures with three-dimensional temperature sensor arrays configured to simulate anatomical geometries such as the gastrointestinal (GI) or respiratory tract.

BACKGROUND

As an example, medical procedures may require energy transfer to and/or from tissue for diagnostic or treatment purposes, such as energy transfer to/from a cryogenic or electromagnetic energy source. Such procedures often use instruments that can inflict unintended harm and destruction of a target biological tissue or collateral tissue, if the depths and patterns of energy transferred and/or the amount of energy emitted to/from such instruments and/or body tissue is not well understood. Since many treatments must be performed within a patient where potential negative effects to biological tissue are not easily observable or measurable in real time, if at all, devices and methods for energy transfer mapping, including mapping of energy transfer from and/or to an instrument and/or body tissue with test specimens of biological tissue or materials that mimic biological tissue, would be beneficial. Such energy transfer mapping devices and methods could be used in instrument design, and development of energy transfer protocols and profiles for procedures, such as a medical procedure, in order to optimize procedure effectiveness, and reduce undesirable procedure outcomes from damage inflicted by energy delivery that is not as expected. It is with these considerations in mind that the improvements of the present disclosure may be advantageous.

SUMMARY

The present disclosure in various embodiments may include devices and methods for mapping of energy transferred from and/or to an instrument, including the depths and patterns of penetration and/or amounts of energy transferred from and/or to an instrument delivered within biological tissue or materials that mimic biological tissue, including within fixtures with three-dimensional temperature sensor arrays configured to simulate anatomical geometries such as the gastrointestinal (GI) or respiratory tract. These tissues and materials may be within fixtures having three-dimensional sensor arrays, such as temperature sensors arranged around a lumen, configured to simulate anatomical geometries such as the GI or respiratory tract.

The present disclosure in various embodiments includes apparatuses, systems and methods for mapping. In one aspect, an exemplary device for mapping may include a first flexible circuit and a plurality of first sensors arranged about an edge of the first flexible circuit. The device may be operable to create a two-dimensional energy map. The device may be operable to create a three-dimensional map. The flexible circuit may be a three-dimensional circuit having a continuous circuit pathway that extends in a first dimension, a second dimension, and a third dimension. The edge of the first flexible circuit may be continuous and may extend in the first dimension, the second dimension, and the third dimension. The sensors may be arranged about the edge in an array with a predetermined pattern that corresponds to specific distances or locations, or both, measured outward from the edge. The plurality of first sensors may include copper-Constantan junction thermocouples. The junction may include a 'T-type' configuration. The plurality of first sensors may include an inner plurality of first sensors disposed on the flexible circuit a first distance from the edge of the first flexible circuit. An outer plurality of first sensors may be disposed on the flexible circuit a second distance from the edge of the first flexible circuit. The first distance may be uniform among the inner plurality of first sensors. The first distance may be non-uniform among the inner plurality of first sensors. The second distance may be uniform among the outer plurality of first sensors. The second distance may be non-uniform among the outer plurality of first sensors. The second distance may be greater than the first distance. The first distance may be about 3 mm. The inner plurality of first sensors and outer plurality of first sensors may each comprise four sensors spaced ninety degrees apart. The inner plurality of first sensors and outer plurality of first sensors may be circumferentially spaced apart from each other about a center point of a circular aperture defined by the edge of the first flexible circuit. The edge may be linear and may extend along a side of the first flexible circuit. The plurality of first sensors may be disposed on the first flexible circuit in columns that are substantially perpendicular to the linear edge. The edge may have a circumference that defines an aperture through the first flexible circuit. The circumference may be circular.

In another aspect, a device may include a second flexible circuit layered in a plane substantially parallel to a plane of the first flexible circuit. The first circuit and second circuit may be arranged along a longitudinal axis extending a length of the device. The planes of the circuits may be normal to the axis. The second flexible circuit may have a plurality of second sensors arranged about an edge of the second flexible circuit. The plurality of second sensors may be aligned along the longitudinal axis with the plurality of first sensors. A gel may be in contact with the edge of the first flexible circuit and in contact with the edge of the second flexible circuit. The first flexible circuit may be connected to the second flexible circuit. The second flexible circuit may be foldable over the first flexible circuit where the second flexible circuit is connected to the first flexible circuit. One or more spacer elements may be disposed between the first flexible circuit and the second flexible circuit. A test specimen of biological tissue may be between the first flexible circuit and the second flexible circuit. The edges of the first flexible circuit and the second flexible circuit may have a circumference that defines a substantially circular aperture. The aperture of each circuit may have a diameter and may be aligned along the longitudinal axis to form a lumen through the circuits. The diameter of the aperture of the first flexible circuit may be different than the diameter of the aperture of the second flexible circuit. A housing may surround the first flexible circuit and the second flexible circuit. The housing may have a top aperture and a bottom aperture. The lumen may be substantially aligned axially with the top aperture and with the bottom aperture. An injector element may be slidingly receivable within the lumen and the top and bottom aperture of the housing. The injector element may have a body. The injector element may have a connection point at a first end of the injector element to receive a gel. One or more outlets may be at a second end of the injector element to allow for the gel to exit the injector element. An injector lumen may be within the body of the injector element and in fluid communication with the connection point and the outlets. The body may have an outer diameter substantially equal to an inner diameter of the lumen extending through the circuits. The injector element may be receivable within the housing leading with the first end through the bottom aperture of the housing. The injector element may include a back stop at the second end that may be further away from the first end than the outlets. The back stop may be configured to prevent the second end of the injector element from translating through the bottom aperture. At least one vent aperture may be in the housing to allow for the gel to exit the housing. A plug-in connector may be in electrical communication with the plurality of first sensors and second sensors. The plug-in connector may extend out of the housing and configured to interface with a console. The console may include a data collection unit and a display.

In another aspect, a mapping device may include a plurality of sensor arrays layered in planes substantially parallel to each other along a longitudinal axis extending a length of the device. The planes of the arrays may be normal to the axis. Each array may have a plurality of sensors arranged about an exposed area. Each exposed area may be a space perpendicular to an end of the sensors in the respective sensor array. A gel may be disposed within each exposed area and about the sensors in the respective sensor array. The exposed area of each sensor array may be an aperture. At least one of the apertures of the sensor arrays may have a different diameter than at least one of the remaining apertures. The apertures of the sensor arrays may be substantially aligned along the longitudinal axis. A gel may be disposed about the sensors. The gel may have a firmness sufficient to define a lumen substantially co-axial with the apertures of each exposed area. A plug-in connector may be in electrical communication between the plurality of sensor arrays. At least one layer of test specimen of biological tissue may be between each array of the plurality of sensor arrays. One or more spacer elements may be between each array of the plurality of sensor arrays. The spacer elements may include a spacer element aperture. The exposed area of each array may be an exposed aperture that may have a diameter smaller than a diameter of the spacer element apertures. At least one depth sensor may be positioned radially farther away from the longitudinal axis than each of the sensors.

In another aspect, a mapping system may include a housing with an aperture at each end of the housing. A plurality of sensor arrays may be layered in planes substantially parallel to each other within the housing along a longitudinal axis extending a length of the housing. The planes of the arrays may be normal to the axis. Each array may have a plurality of sensors arranged about an aperture extending through the array. A gel may be disposed about the sensors. The gel may define a lumen therethrough that is substantially aligned with the aperture of each sensor array along the longitudinal axis. An injector element may be slidingly receivable within the lumen and the top and bottom aperture of the housing. The injector element may have a body including a connection point at a first end of the injector element to receive a gel. One or more outlets may be at a second end of the infector element to allow for the gel to exit the injector element. An injector lumen may be within the body of the injector element and may be in fluid communication with the connection point and the outlets. The body may have an outer diameter substantially equal to a diameter of the lumen extending through the circuits. The injector element may be receivable within the housing leading with the first end through the bottom aperture of the housing. The injector element may further comprise a back stop at the second end that may be further away from the first end than the outlets. The back stop may be configured to prevent the second end of the injector element from translating through the bottom aperture. At least one vent aperture may be in the housing to allow for the gel to exit the housing. At least one sensor connector may be in communication with the plurality of sensor arrays and extending out of the housing.

In another aspect, a mapping device may include a plurality of connected flexible circuits. A sensor array may be integrated on each flexible circuit and may comprise a plurality of sensors adjacent to an aperture. Each array and flexible circuit may be electrically connected to at least one other array and flexible circuit. The flexible circuits may be connected in a pattern such that the sensor arrays can be folded on top of each other. A plurality of spacer elements may be disposed on each flexible circuit. Each of the plurality of spacer elements for a respective sensor array may have a spacer element aperture axially aligned with the aperture of the corresponding sensor array. A diameter of each spacer element aperture may be larger than a diameter of the aperture of the corresponding sensor array. Each sensor array may have at least one vent aperture parallel to the aperture between the aperture and the spacer element aperture. A mapping device may include a plurality of connected flexible circuits. A sensor array may be integrated on each flexible circuit comprising a plurality of sensors adjacent to an aperture. Each array and flexible circuit may be electrically connected to at least one other array and flexible circuit. Each circuit of the plurality of circuits may be deposited in a layer using additive manufacturing to form the device.

In another aspect, a method for developing a treatment for a region of tissue in a body lumen of patients may include creating a map with an instrument design in a test fixture having a three-dimensional sensor array. The fixture may include a simulated lumen configuration and material that approximates the respective body lumen and tissue of the patients. The method may include establishing a range of treatment protocol for the instrument design based on the map. The method may include instructing the treatment of the region of tissue of the patients, within the range of the treatment protocol, using an instrument comprising the instrument design. The sensor array may include at least one inner sensor at a first depth away from an edge defining a circumference of the simulated lumen and may include at least one outer sensor at a second depth further away from the edge than the first depth. The test fixture may include a plurality of flexible circuits. Each flexible circuit may include the at least one inner and outer sensor. The circuits may be layered in planes. The planes may extend along and normal to a longitudinal axis of the test fixture. The simulated lumen configuration may be defined by the plurality of edges within the plurality of layered flexible circuits. Creating the map may include measuring an amount of energy transfer for the treatment protocol and may include calculating a total of the amount of energy transfer over a selected time of a treatment.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 illustrates a cross-section view of a flexible circuit construction with a T-type thermocouple junction, in accordance with an embodiment of the present disclosure.

FIG. 6 illustrates a flexible circuit with sensor arrays arranged in a concentric layered formation, in accordance with an embodiment of the present disclosure.

DETAILED DESCRIPTION

Figure 2A:
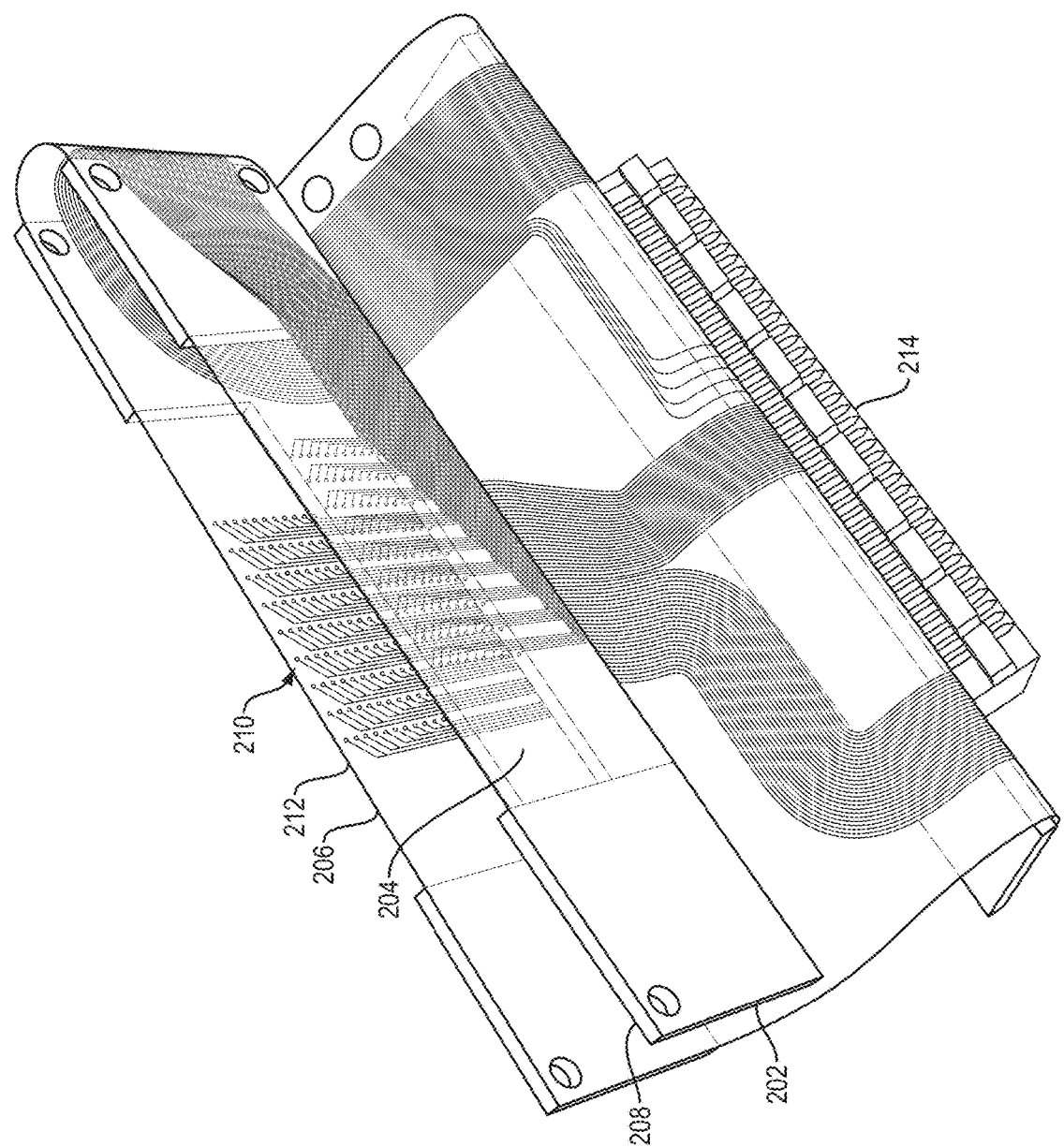
FIG. 2A illustrates a flexible circuit construction with a sensor array arranged in rows and columns, in accordance with an embodiment of the present disclosure.

The present disclosure is not limited to the particular embodiments described. The terminology used herein is for the purpose of describing particular embodiments only, and is not intended to be limiting. Unless otherwise defined, all technical terms used herein have the same meaning as commonly understood by one of ordinary skill in the art to which the disclosure belongs.

Although embodiments of the present disclosure are described with specific reference to energy transfer mapping with flexible circuits having sensor arrays and apertures layered to create a lumen that simulates the upper and lower GI tracts and respiratory system, including for use in testing the depths and patterns and amount of energy transferred to and/or from cryoablation systems within tissue that mimics body tissue, it should be appreciated that such systems and methods may be used in a variety of configurations of the flexible circuits, with a variety of instruments, a variety of fluids, a variety of energy delivery modalities, and for a variety of other body passageways, organs and/or cavities, such as the vascular system, urogenital system, lymphatic system, neurological system and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the term "distal" refers to the end farthest away from the medical professional when introducing a device into a patient, while the term "proximal" refers to the end closest to the medical professional when introducing a device into a patient.

As used herein, the term "gel" may include a flowable substance that can be cured into a solid or semi-solid. "Gel" may include biological tissues or materials. "Gel" may include a fluid in a liquid state. A gel may have a firmness sufficient to allow it to be cured into a form that defines a lumen. Biological tissue may comprise harvested grafts of tissue or simulated tissue that mimics biological material. A gel may comprise silicone, nylon, urethane, or the like. Gel materials may be selected with particular physical properties such as conductivity, specific heat, electrical resistance, elasticity, speed of sound, or the like, useful for different applications for mapping energy from a device.

Embodiments of the present disclosure may include one or more flexible circuits, each having a sensor array such that the device may map, measure, record, and/or report two-dimensional and three-dimensional energy transfer from and/or to an instrument, e.g., from and/or to a cryospray probe. Devices and methods for mapping of energy transfer from and/or to an instrument may include the depths and patterns of penetration and/or amounts of energy transferred to and/or from biological tissue or materials that mimic biological tissue. These tissues and materials may be within fixtures having three-dimensional sensor arrays, such as temperature sensors arranged around a lumen, configured to simulate anatomical geometries such as the GI or respiratory tract.

In various embodiments described here or otherwise within the scope of the present disclosure, energy transfer may be mapped, measured, recorded, and/or reported. Additionally, various embodiments may include sensors for measuring or mapping other quantities such as energy (i.e. not a transfer of energy) or field quantities. For example, various embodiments may map, measure, record and/or report energy (using, e.g., thermocouples), or field quantities (by including, e.g., one or more sensors that measure stress, strain, pressure, or the like).

The devices and methods of the present disclosure may be used with cryoablation systems to measure and display energy transfer maps that model the effects of cryospray gases (hereafter referred to as "cryospray") within a body lumen. Exemplary cryoablation systems with which the present disclosure may be implemented include, but are not limited to, those systems described commonly owned U.S. Pat. Nos. 9,820,797, 9,301,796 and 9,144,449, and U.S. patent application Ser. Nos. 11/956,890, 12/022,013, and 14/012,320, each of which are herein incorporated by reference in their entirety.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Embodiments of the present disclosure may be used to create energy transfer maps from sensor arrays arranged to simulate body lumens and mimic biological tissues. A mapping of the energy measurements may illustrate a two dimensional or three-dimensional model of energy delivered to tissue from a particular instrument design operating with a certain treatment protocol during the course of a procedure time. The results from the mapping may highlight how changes in the instrument design and/or the treatment protocol might alter the energy transfer profile in a way that the design and protocol can be optimized for a given procedure. The transfer of energy may be measured in a biological tissue or a material that mimics biological tissue. A biological tissue or a material that mimics biological tissue, e.g. a gel, may be disposed about and/or within an exposed area and/or edge and about the sensors in their respective sensor array. Sensor arrays may be arranged in layers and spaced apart in a fixture to create a three-dimensional model. Sensors may have a predetermined pattern that corresponds to specific distances or locations, or both, measured outward from the edge of the circuit. The sensor arrays may measure attributes of energy transfer within the biological or gel material about the flexible circuits.

Embodiments may include energy transfer mapping devices, which are flexible circuits with arrays of sensors arranged thereon. The circuits may be layered to create a three-dimensional fixture, e.g., with a through-lumen that simulates a lumen of a patient's body. The sensors may be thermocouples. An example of a thermocouple includes two different metals connected with a varying voltage between the two, reflecting a proportional temperature. Thermocouples may be T-type thermocouples (e.g., copper-constantan junctions). Referring to FIG. 1, an embodiment of a thermocouple construction is illustrated. The construction shown is fabricated with a laminate of Constantan (Cu—Ni) foil 102 (e.g., about 0.001 in. thick), a first layer of pressure sensitive adhesive (PSA) 104 (e.g., about 0.001 in. thick), a polyimide film 106 (e.g., about 0.001 in.), a second layer of pressure sensitive adhesive 108 (e.g., about 0.001 in. thick), and a copper foil 110 (e.g., about 1 ounce). A drill (e.g., a computer numerical controlled drill) or a laser may be used to bore a hole 112 (e.g., down to about 0.005-in. diameter for a drill and down to about less than 0.001-in. diameter for a laser) in the locations where all copper-Constantan junctions will be made. Both sides of the layered thermocouple may be imaged with a circuitry pattern mask, and then acid etched to remove the unmasked metal. The drilled hole 112 junctions may then be pad plated with copper 114 to join the copper 110 with the Constantan foil 102, resulting in a precisely located (e.g., about ±0.0001 in.) thermocouple junction. The circuit may then be plated with electroless nickel immersion gold (ENIG) 116 to protect the copper circuitry from corrosion. A coverlay 118 (e.g., about 0.0005 in. thick) may then be applied with final layers of pressure sensitive adhesive 120 (e.g., about 0.0001 in. thick). The hole 112 junctions are exposed by creating, e.g., laser cutting, openings 122 in the coverlay 118. Excess substrate and coverlay 118 are cut away using, for example, a laser cutter. The openings 122 exposing the gold plating 116 allow for materials that mimic body tissue (e.g., gel, biological tissue, etc.) to make contact with the gold plating 116. Finally, the top (copper foil 110 side) surface may be silkscreened to provide identifying information such as lumen size and part number. In various embodiments, the sensor may instead be a resistance temperature detector (RTD), a diode, a capacitive sensor, or the like.

In various embodiments of energy transfer mapping devices, a flexible circuit may have a plurality of sensors. The sensors may be arranged in sensor arrays about an edge of the flexible circuit and/or arranged about an exposed area. The edge may be one or more inner edges of a circuit. The edge and/or exposed area may define an aperture that may be circular. The edge and/or exposed area may be a space perpendicular to an end of the sensors in their respective sensor array. A perimeter of an edge may define the aperture through a flexible circuit. An inner plurality of sensors may be disposed on a flexible circuit at a first distance from the edge, and an outer plurality of sensors may be disposed on the flexible circuit at a second distance from the edge. The first and second distances may be uniform or non-uniform among the inner and outer plurality of sensors. Multiple circuits, each having an aperture, may be layered together such that the apertures are axially aligned, creating a lumen. A sensor array may be disposed along a portion of an edge, e.g., half of the edge defining a circular circumference, so as to capture a portion of a circumferential profile of energy transfer between an instrument and a tissue.

Figure 2B:
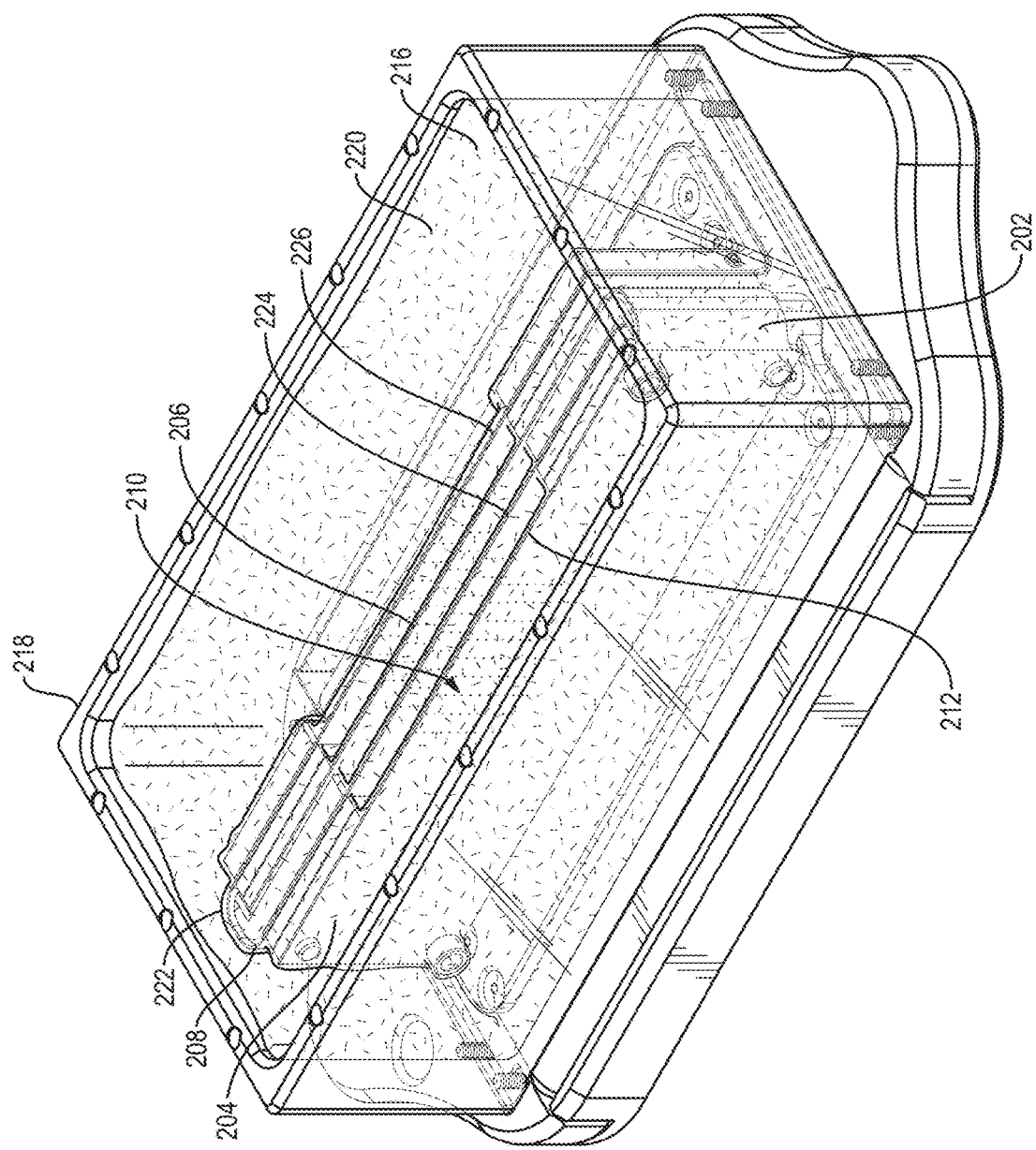
FIG. 2B illustrates an isometric view of layered flexible circuits with sensor arrays such as the construction of FIG. 2A arranged in a fixture, in accordance with an embodiment of the present disclosure.
Figure 2C:
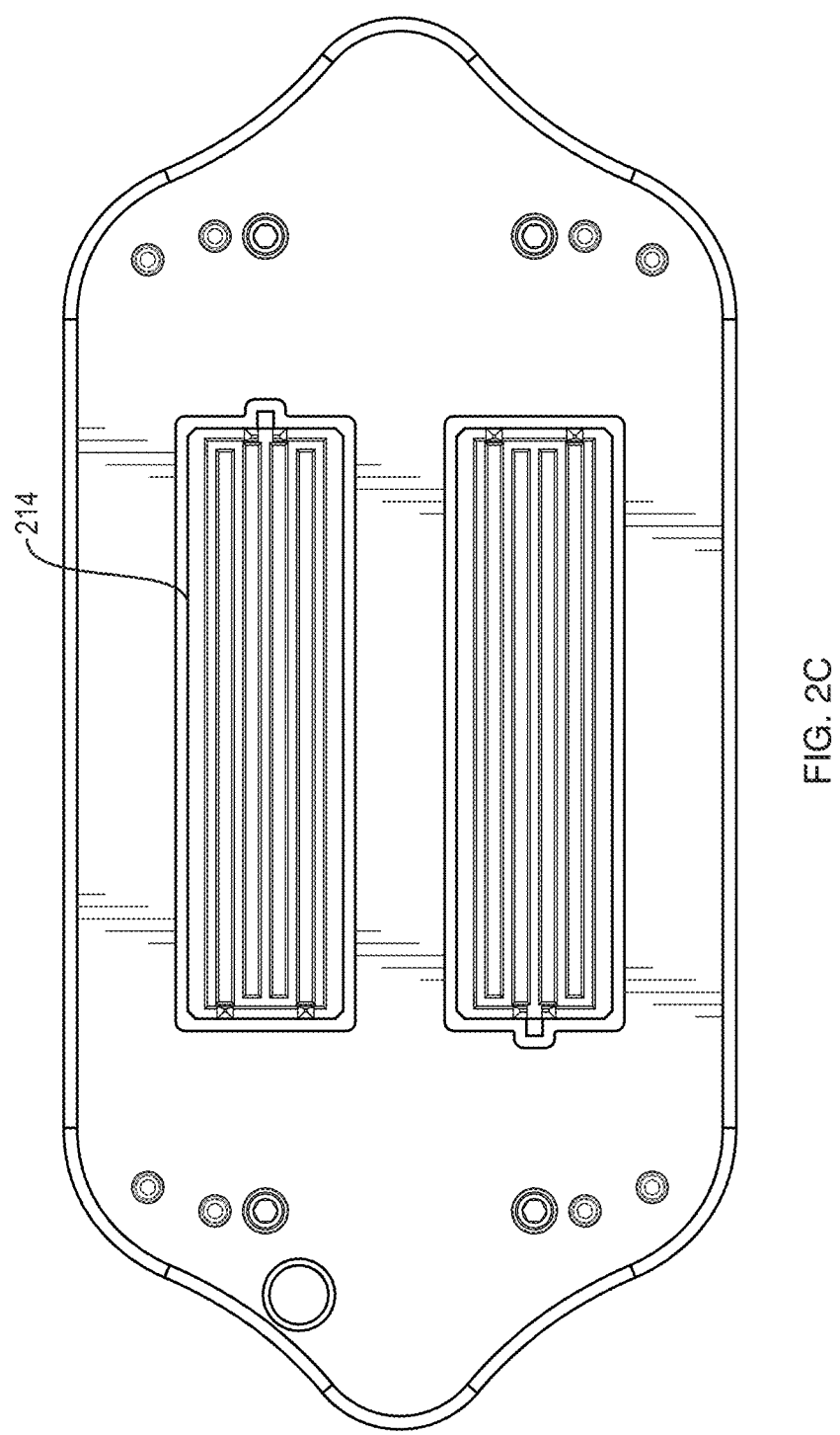
FIG. 2C illustrates a bottom view of the fixture of FIG. 2B.

Referring to FIGS. 2A-2C, an embodiment of an energy transfer mapping device according to the present disclosure is illustrated, which includes a fixture with a sensor array. The fixture has a substantially flat surface 220 for mapping energy transfer in a biological or material that is contained within the fixture. A first substrate 202 is folded over to create a first flexible circuit 204 and a second flexible circuit 206 that are connected. Spacer elements 208 are included to space, flatten, and stiffen the layers of the first circuit 204 and the second circuit 206. The spacer elements 208 may also serve to keep the layers of the first circuit 204 and the second circuit 206 parallel to each other. A sensor array 210 is disposed on each of the first 204 and second 206 circuits. The sensor array is arranged about an edge 212 of the flexible circuits 204 and 206. The edge 212 extends along a side of the first substrate 202. The sensor arrays 210 are arranged in columns that are substantially perpendicular to the edge 212 of each of the flexible circuits 204 and 206. A connecter 214 allows for electrical communication between the sensor arrays 210 and is configured to interface with a console that may include a data collection unit and display.

Referring to FIG. 2B, an embodiment of an energy transfer mapping device according to the present disclosure is illustrated, which includes a second substrate 222 similar to the first substrate 202, folded over to create a third flexible circuit 224 and a fourth flexible circuit 226 that are connected. The second substrate 222 is layered with the first substrate 202. The third flexible circuit 224 is layered between the first flexible circuit 204 and the second flexible circuit 206, while the second flexible circuit 206 is layered between the third flexible circuit 224 and the fourth flexible circuit 226. Alternatively, a single longer substrate might be folded over four times to create four-layers of flexible circuits. The circuits may be layered in configurations such that the flexible circuit(s) do not bend with too small of a radius, helping to avoid damage to and/or poor performance of the flexible circuit(s). Additionally, various numbers of layers of flexible circuits, or configurations other than layers, and/or with different numbers, configurations and arrangement of sensors thereon, are contemplated within the present disclosure as suitable for desired applications and uses of test fixtures. Referring again to FIG. 2B, a sensor array 210 is disposed on each of the first 204, second 206, third 224, and fourth 226 flexible circuits. The sensor arrays 210 are arranged in columns that are substantially perpendicular to a linear edge 212 of each of the flexible circuits 204, 206, 224, and 226. Although other materials may be used, a gel 216 (e.g., a water-based gel) is shown applied within the housing 218 that covers the flexible circuits 204, 206, 224, and 226. The gel 216 fills the space in between the flexible circuits 204, 206, 224, and 226 and creates a gel surface 220 above the edges 212. The gel surface 220 is perpendicular to the columns of sensors 210. The connectors 214 in FIG. 2C allow for electrical communication between the sensor arrays 210 and are configured to interface with a console. One connector 214 interfaces the first 204 and second 206 circuits with a console while the other connector 214 interfaces the third 224 and fourth 226 circuits with the console. A medical instrument may be used on the gel surface 220 with the gel surface 220 simulating a substantially flat portion of biological tissue. The sensor arrays 210 measure properties (e.g., depth and patterns of energy penetration, amount of energy, temperature, etc.) within the surrounding gel 216 as a medical instrument transfer energy to and/or from the gel surface 220. The sensor arrays 210 are arranged in columns in order to measure the properties at various depths within the gel 216 (i.e., closer and farther from the gel surface 220). The inner plurality of sensors of the sensor arrays 210 closest to the edges 212 and the gel surface 220 will measure substantially topical properties of energy transfer within the gel 216. An outer plurality of sensors of the sensor arrays 210 that are farther from the edges 212 and the gel surface 220 will measure properties of energy transfer deeper within the gel 216. A higher number and clustering of the sensors of the sensor arrays 210 may allow for a higher resolution of property measurements within the gel 216. Additionally, the substantially flat gel surface 220 allows measurements from various angles between the gel surface 220 and the medical instrument. For example, a medical instrument applying energy in a radial pattern to the gel surface 220 would result in measurement angles of transferred energy perpendicular to the gel surface, as well as measurement angles of transferred energy that are slanted to the gel surface 220, in accordance with the angles of the radial spray pattern of the particular instrument, with the sensors spread out farther from the medical instrument along the edges 212 providing a measure of how the transferred energy profile of the instrument in the gel 216 varies across the spray pattern. These measurements from a substantially flat gel surface 220 and a radial treatment pattern allow for various measurement angles depending on the orientation of the instrument with respect to the gel surface 220. Conversely a cylindrical gel surface, e.g., for a medical instrument having a radial treatment pattern inserted therein, only allows for limited orientation of the instrument within the lumen of the cylinder. Although a water-based gel 216 is depicted, various other test specimens of materials that mimic biological tissue may be used instead (e.g., test specimen of biological tissue layered on, around, among, and/or between the flexible circuits 204, 206, 224, and 226).

Figure 3A:
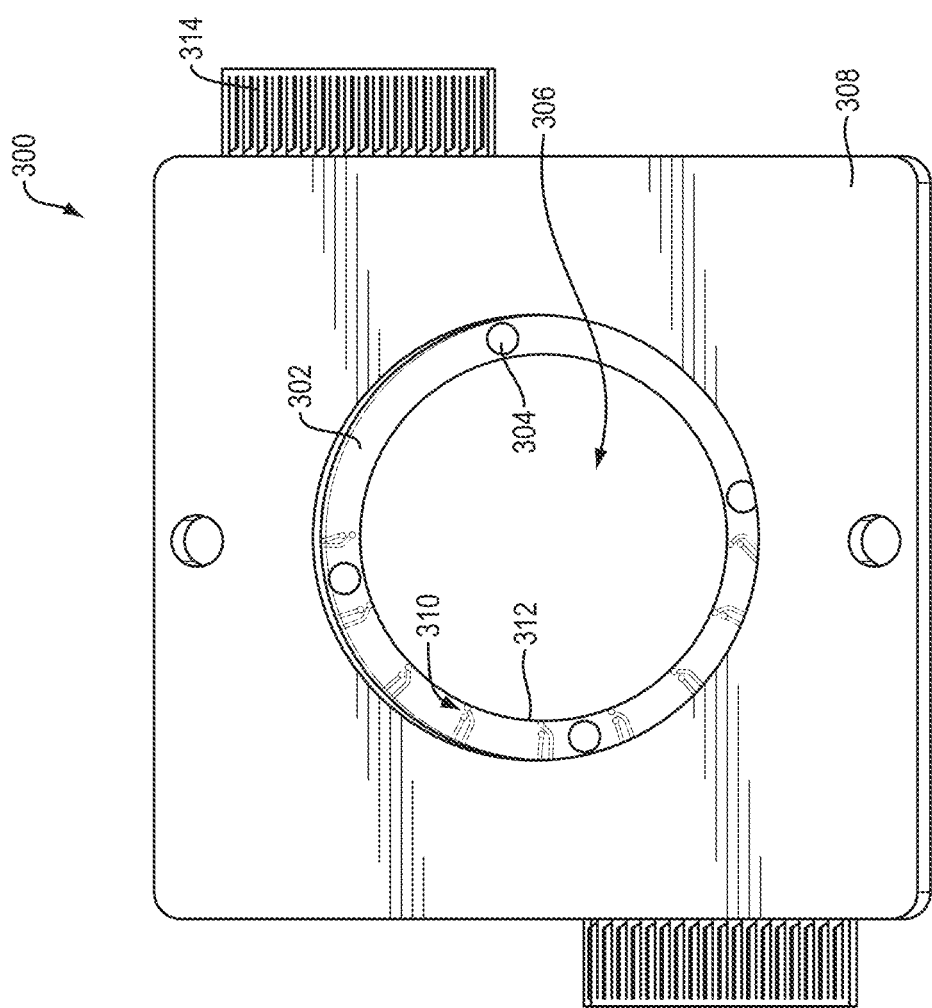
FIG. 3A illustrates a sensor array configuration on a flexible circuit, in accordance with an embodiment of the present disclosure.
Figure 3B:
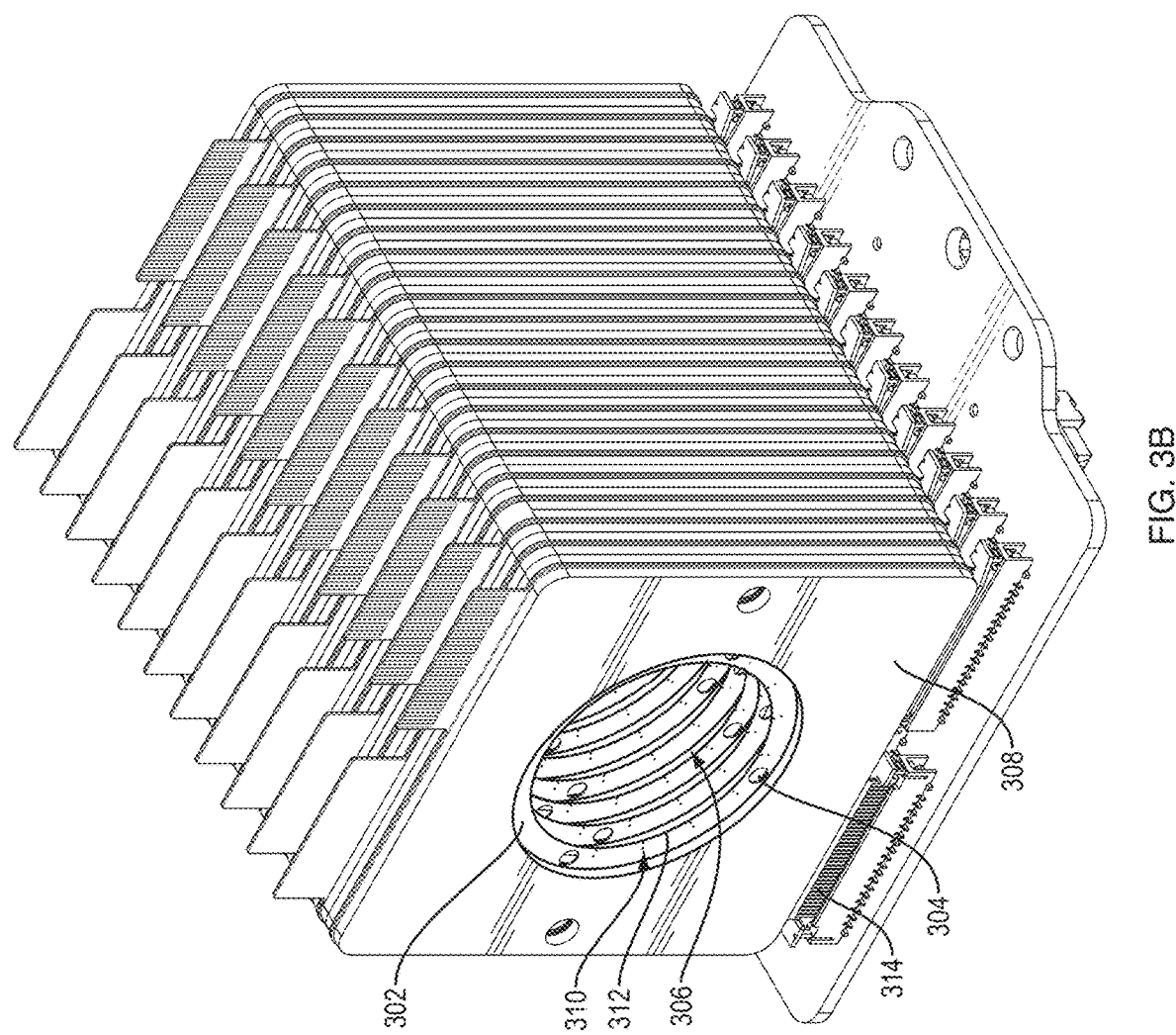
FIG. 3B illustrates multiple flexible circuits with sensor arrays such as the construction of FIG. 3A aligned in a fixture with a through-lumen, in accordance with an embodiment of the present disclosure.
Figure 4A:
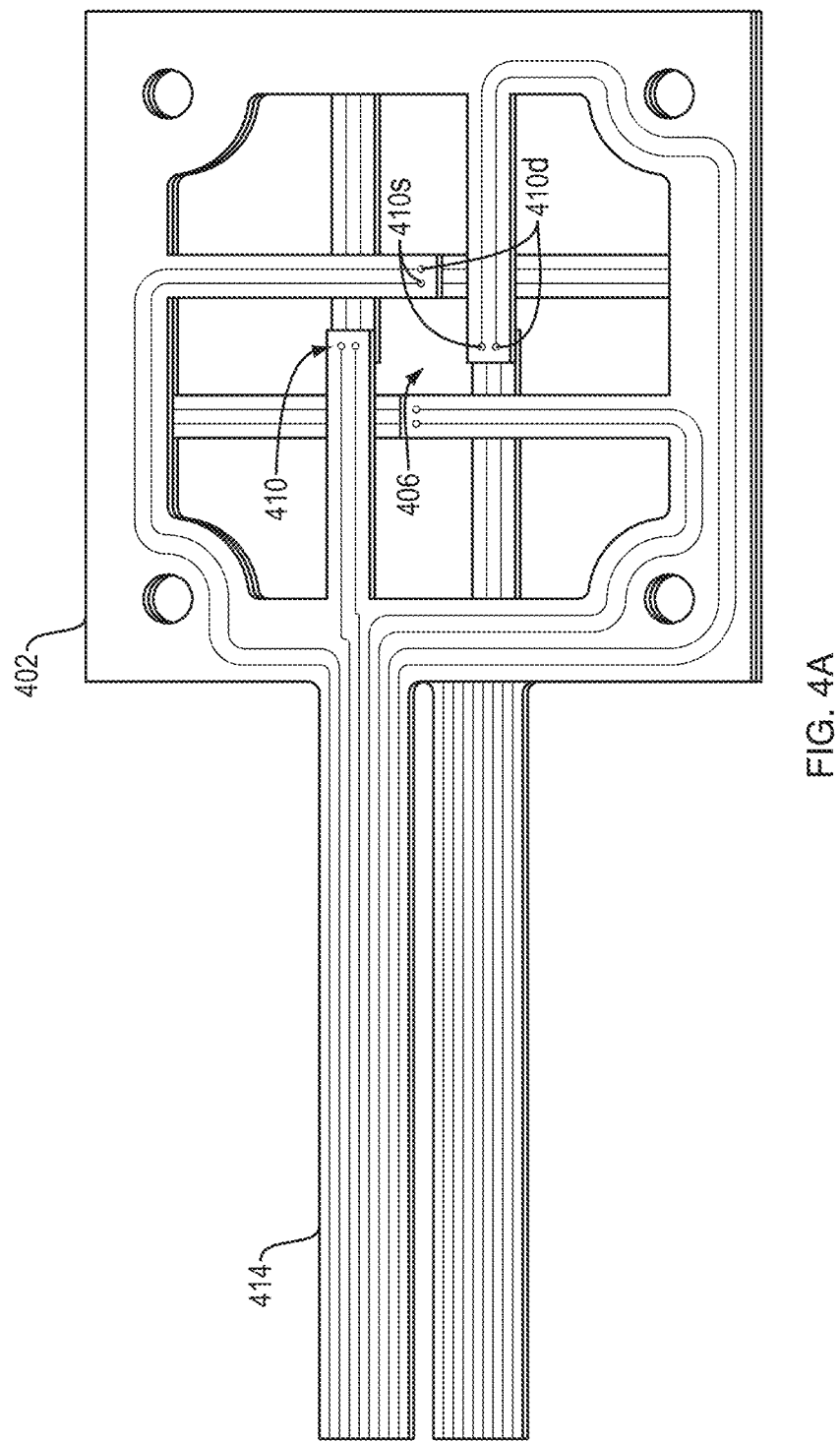
FIG. 4A illustrates two layered flexible circuits with sensors, in accordance with an embodiment of the present disclosure.
Figure 4B:
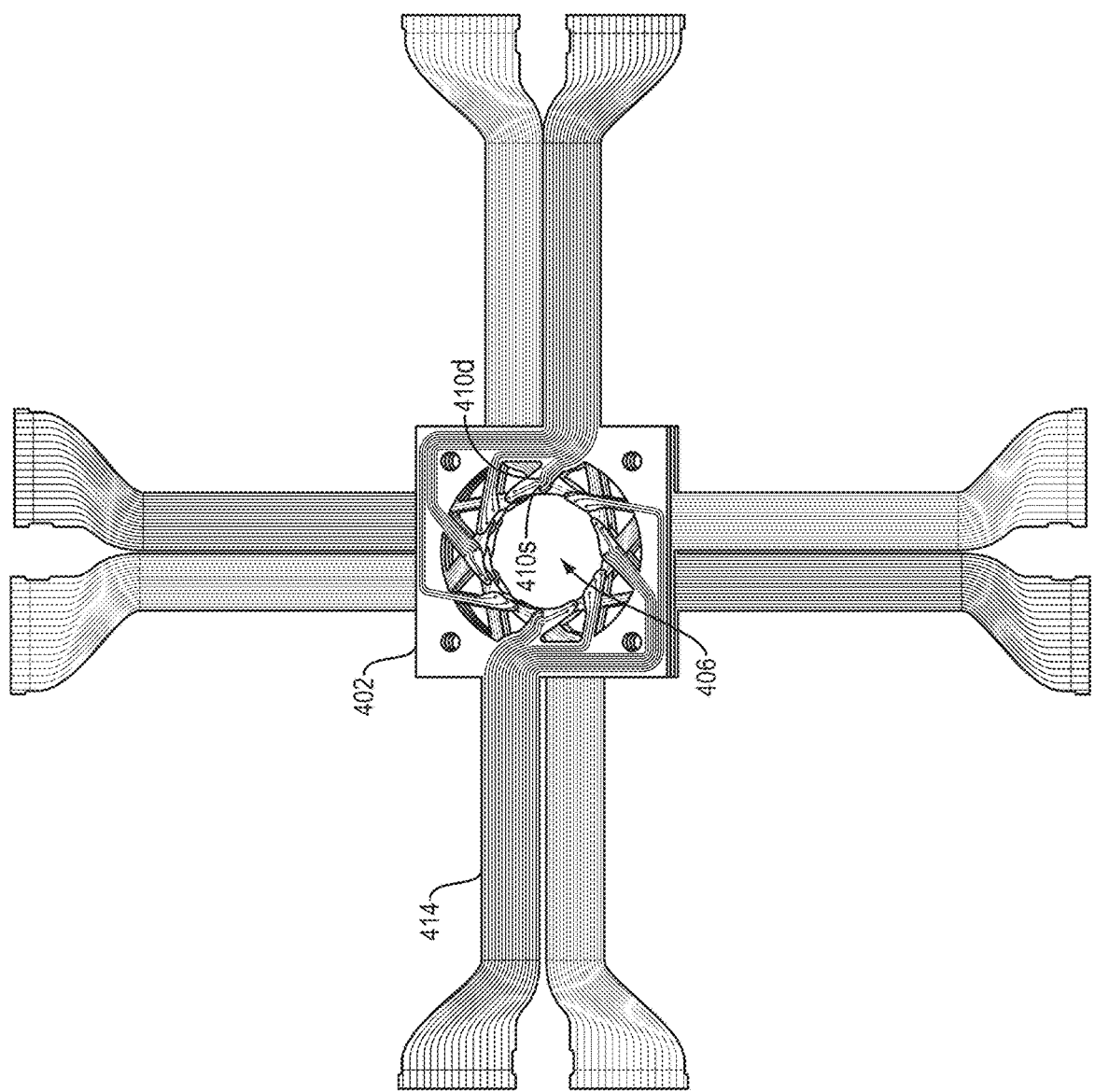
FIG. 4B illustrates a series of layered flexible circuits with sensors such as the construction of FIG. 4A, in accordance with an embodiment of the present disclosure.
Figure 4C:
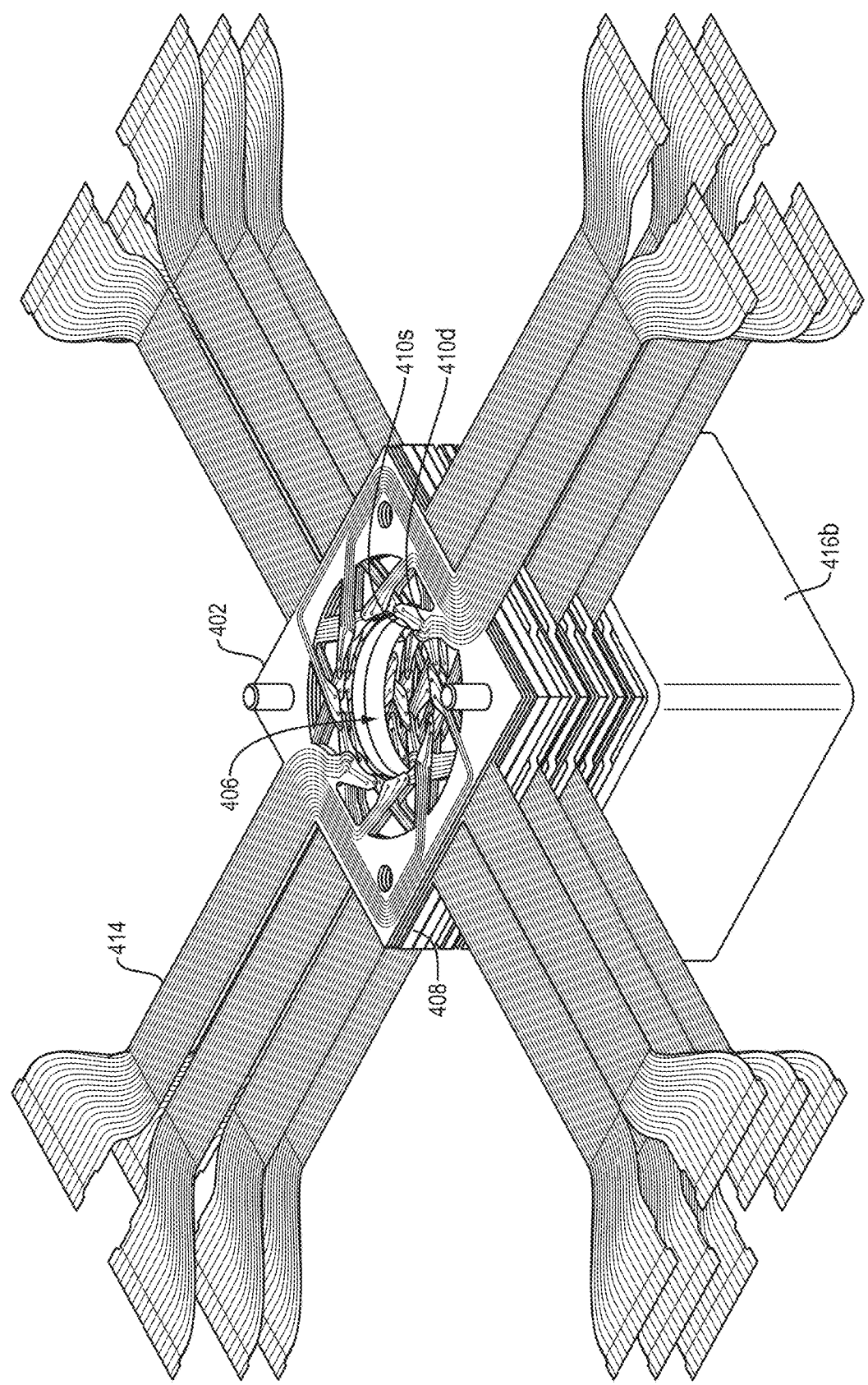
FIG. 4C illustrates an isometric view of the circuits of FIG. 4B arranged in a partial fixture, in accordance with an embodiment of the present disclosure.
Figure 4D:
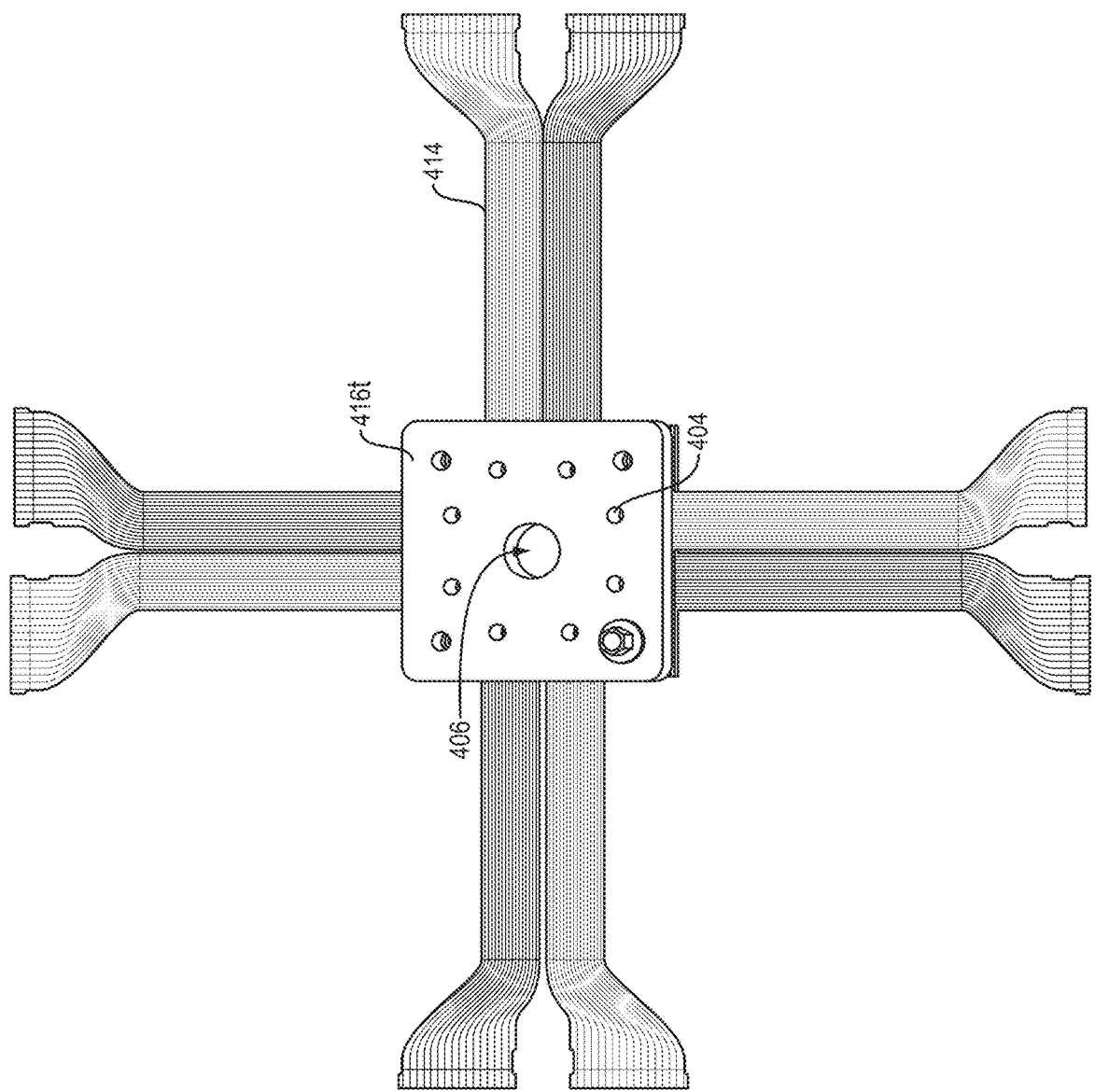
FIG. 4D illustrates the circuits of FIGS. 4B and 4C arranged in a completed fixture, in accordance with an embodiment of the present disclosure.

Referring to FIGS. 3A-3B, an embodiment of a device for energy transfer mapping is depicted, which includes a flexible circuit assembly 300 with a flexible circuit 302 between two spacer elements 308. The spacer elements 308 may space, flatten, and stiffen the flexible circuit 302. The spacer elements 308 may also serve to keep the flexible circuits 302 of multiple flexible circuit assemblies 300 parallel to each other. The flexible circuit 302 has an aperture 306 defined by an edge 312 through the flexible circuit 302. The aperture extending through the spacer elements 308 has a larger diameter than that of the aperture 306 in the flexible circuit 302 in order to expose an array of sensors 310 on the flexible circuit 302. The array of sensors 310 are disposed on the flexible circuit 302 about the edge 312 defining the aperture 306. One or more connectors 314 allow the flexible circuit 302 to interface with a console. The connecter 314 allows for electrical communication between the sensor arrays 310 and is configured to interface with a console that may include a data collection unit and display. Multiple flexible circuits 302 may be layered with a plane of each of the circuits 302 parallel to each other (e.g., plugged into a board 316, as shown in FIG. 3B). and extending along a longitudinal axis of a fixture (e.g., board 316), such that the aligned apertures 306 form a lumen through the multiple flexible circuits 302. A substance that mimics body tissue (e.g., gel, test specimens of biological tissue, etc.) may be disposed about the apertures 306 defining the lumen and amongst the sensors 310 to simulate tissue within a body lumen. If the board includes a housing around the circuits 302, and a flowable, settable, gel is used, the vents 304 may allow for excess gel to travel between flexible circuits 302 as as the gel is injected or otherwise inserted about the lumen created by the apertures 306.

Referring to FIGS. 4A-4D, an embodiment of a device for energy transfer mapping according to the present disclosure is illustrated, which includes two flexible circuits 402 with edges defining a lumen 406. A sensor array including an inner plurality of sensors 410s and an outer plurality of sensors 410d surround the lumen 406. The sensors 410s and 410d extend toward the lumen 406 from the outer portion of the flexible circuit 402. A connector 414 allows the circuits 402 to interface with a console. The connecter 414 allows for electrical communication between the sensor arrays 410 and is configured to interface with a console that may include a data collection unit and display. The circuits 402 can be layered to increase the depth of the lumen 406 and the number of sensors 410s and 410d. One of the two circuits 402 may be flipped over (e.g. with the connector 414 still extending in the same direction as in FIG. 4A), resulting in alternating orientations of the flexible circuits 402 in order stagger the locations of the sensors 410s and 410d in a pattern. The sensors 410 may have a predetermined pattern that corresponds to specific distances or locations, or both, measured outward from the edge of the circuit 402. Similar to the arrangement of the circular aperture in FIGS. 3A-3B, the sensors may be about a center point of a circular aperture defined by the square (e.g., FIG. 4A) or circular (e.g., FIG. 4B) edges of the flexible circuits 402. For example, the inner sensors 410s are circumferentially spaced ninety degrees apart from each other and about 3 millimeters from a center point of the lumen 406 created by the inside edge of the flexible circuit 402. The outer sensors 410d are circumferentially spaced ninety degrees apart from each other. Spacer elements 408 may be used to space, flatten, and/or stiffen the flexible circuits 402. The spacer elements 408 may also serve to keep the circuits 402 parallel to each other. The circuits 402 and spacer elements 408 are layered on a jig bottom 416b (e.g., FIG. 4C). The jig top 416t shown in FIG. 4D compresses the layered circuits 402 and spacer elements 408 onto the jig bottom 416b. The jig bottom 416b and jig top 416t with a plurality of flexible circuits 402 extending therebetween form the lumen 406 from the aligned apertures. The jig top 416t includes vents 404 to allow excess material used to mimic biological tissue (e.g., gel) to ventilate when the material is inserted into the lumen 406. Such circuits 402 may flex with a gel disposed about the lumen 406 as the gel may be flexed, deformed, or otherwise manipulated during a procedure.

Figure 5A:
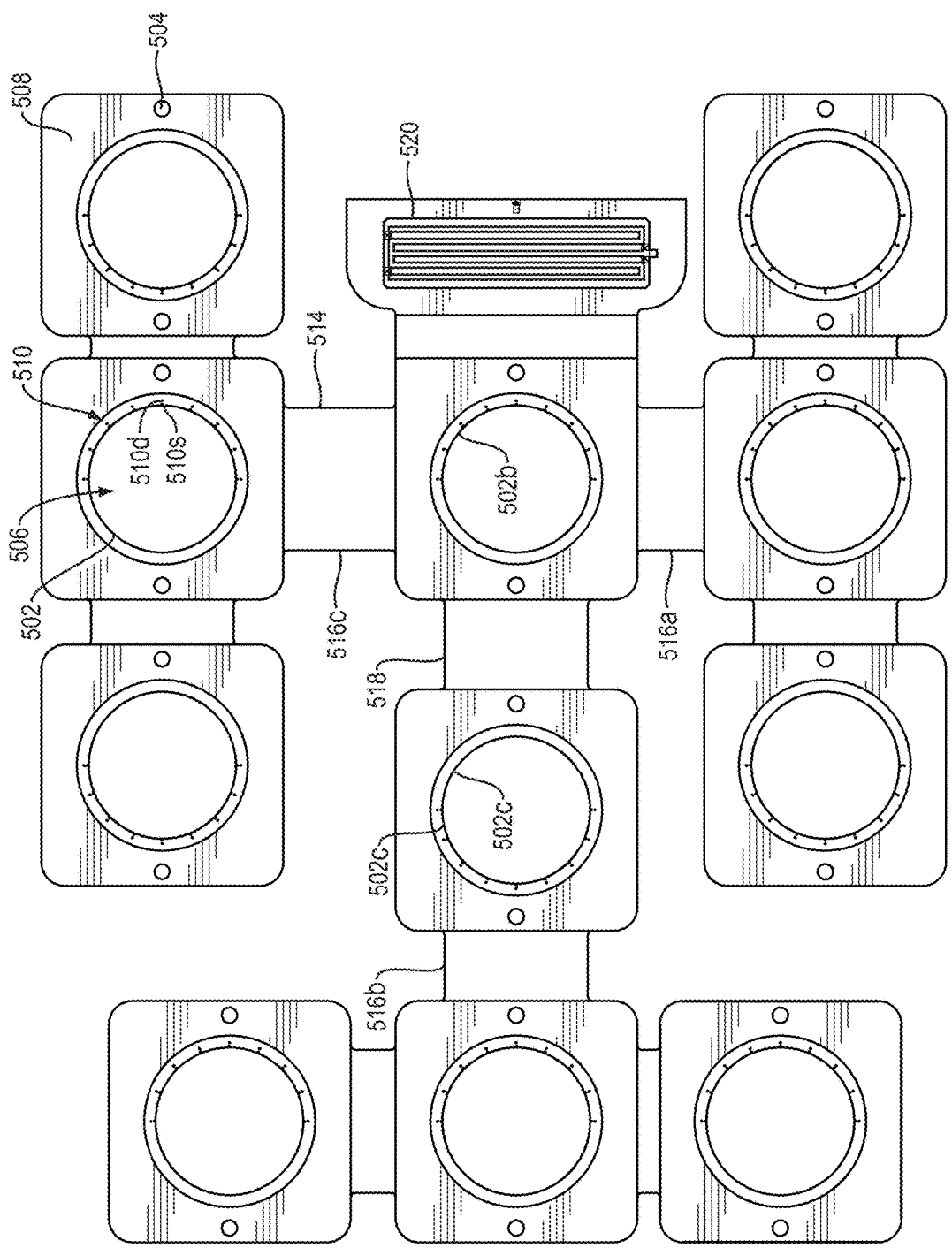
FIG. 5A illustrates an arrangement of connected flexible circuits with sensor arrays, in accordance with an embodiment of the present disclosure.
Figure 5B:
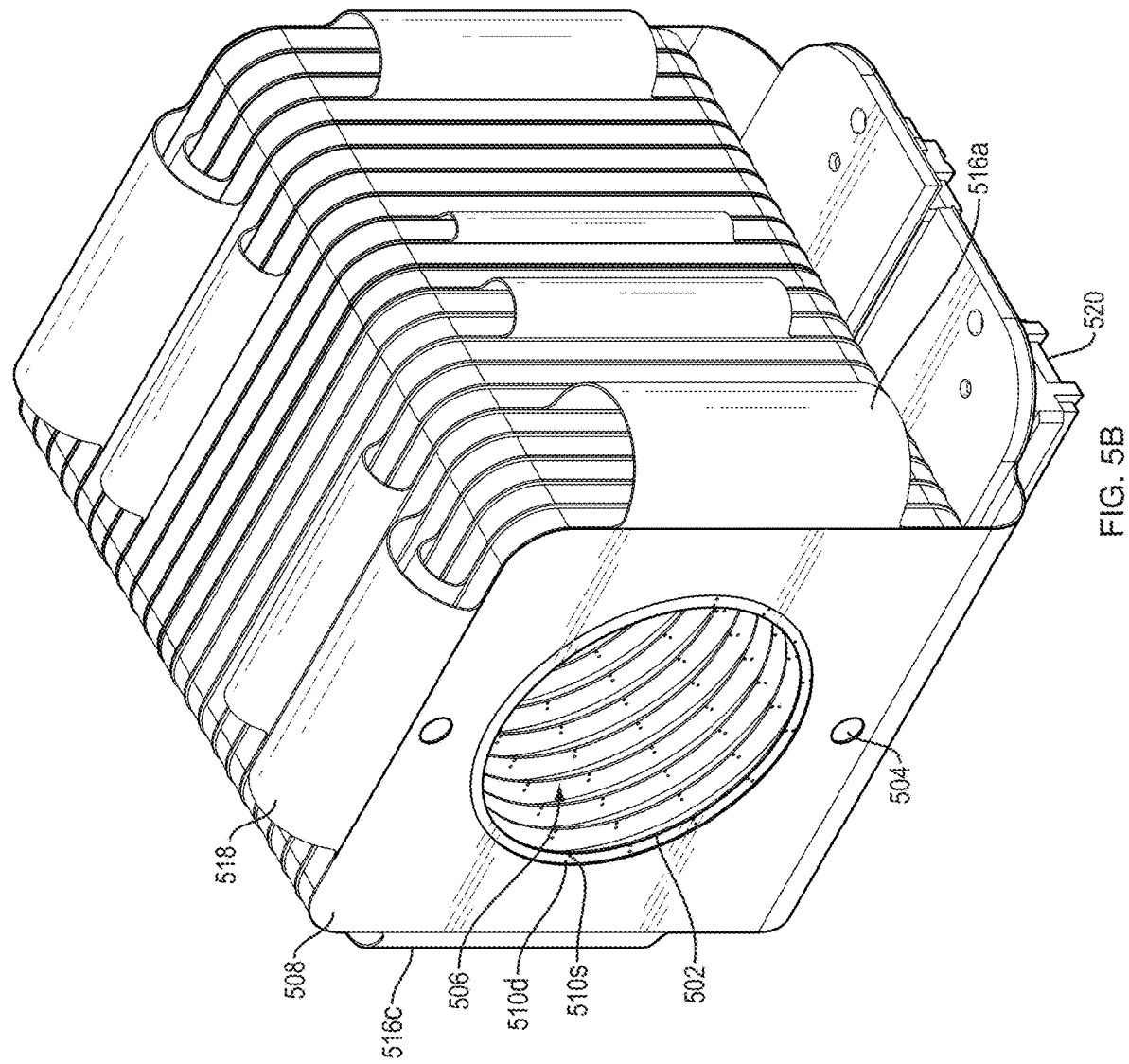
FIG. 5B illustrates the arrangement of FIG. 5A layered flexible circuits to create a fixture with a through-lumen, in accordance with an embodiment of the present disclosure.

Referring to FIGS. 5A-5B, an embodiment of an energy transfer mapping device according to the present disclosure is illustrated, which includes multiple flexible circuits 502 having an aperture 506 defined by an edge. A sensor array 510, including an array of a plurality of inner sensors 510s and outer sensors 510d, are arranged about the edge 502 of each flexible circuit 502. Multiple connectors 514 allow for the multiple flexible circuits 502 to physically connect to adjacent circuits, and electrically connect all to each other and to a plug 520. The connecters 514, and also the plug 520, allow for electrical communication between the sensor arrays 510 and are configured to interface with a console that may include a data collection unit and display. This setup allows the single plug 520 to electrically communicate with all of the sensor arrays 510. The flexible circuits 502 when folded together (e.g, FIG. 5B), are layered together with a plane of each circuit 502 substantially parallel to a plane one or more of the adjacent flexible circuits 502. The flexible circuits 502 in FIG. 5B are arranged along a longitudinal axis extending a length of the fixture with the planes of the circuits normal to the axis to form a lumen out of the aligned apertures 506 and parallel sensor arrays 510 of the circuits 502 layered on top of each other. FIG. 5B illustrates the flexible circuits 502 of FIG. 5A arranged adjacently together, extending the multiple apertures 506 into the lumen. The flexible circuits 502 are layered substantially parallel to each other normal to the longitudinal axis extending along the device and through the lumen created by the apertures 506. The flexible circuits 502 are connected in a pattern such that the sensor arrays 510 can be folded on top of each other. Although two flexible circuits 502 are illustrated in FIG. 5B, any number of circuits 502 may be layered, e.g., 1, 3, 4, etc. FIG. 5A illustrates a first branch 516a of the flexible circuits 502 that is a connector 514 from a central flexible circuit 502b to another flexible circuit 502. This first branch 516a includes three flexible circuits 502. The three flexible circuits 502 of the first branch 516a may be layered such that the aperture 506 of each of the three circuits 502 of the first branch 516a are substantially axial with respect to each other. The three circuits 502 of the first branch 516a may be layered in any order. The three circuits 502 of the first branch 516a may be folded with the central circuit 502b, and any other circuits 502 (e.g., of other branches), such that the spacer elements 508 and circuits 502 are substantially parallel with each other, and the apertures 506 are substantially axial with each other. Similarly, a second branch 516b that is a connector 514 from a connector flexible circuit 502c to another flexible circuit 502. This second branch 516b includes three circuits 502. The three circuits 502 of the second branch 516b may be layered such that the aperture 506 of each of the apertures 506 of the three circuits 502 of the second branch 516b are substantially axial with respect to each other. The three circuits 502 of the second branch 516b may be layered in any order. The three circuits 502 of the second branch 516b may be layered with the connecting sensor array 516c such that the spacer elements 508 and circuits 502 are substantially parallel with each other, and the apertures 506 are substantially axial with each other. The three circuits 502 of the second branch 516b along with the connecting flexible circuit 502c may be layered with the central flexible circuit 502b, and any other circuits 502 (e.g., of other branches 516a and 516c), such that the spacer elements 508 and circuits 502 are substantially parallel with each other, and the apertures 506 are substantially axial with each other. A third branch 516c that is a connector 514 from the central flexible circuit 502b to another circuit 502. The third branch 516c includes three circuits 502. The three circuits 502 of the third branch 516*c* may be layered such that the apertures 506 of each of the three circuits 502 of the third branch 516*c* are substantially axial with respect to each other. The three circuits 502 of the third branch 516*c* may be layered in any order. The three circuits 502 of the third branch 516*c* may be layered with the central circuit 502*b*, and any other circuits 502 (e.g., of other branches 516*a* and 516*b*), such that the spacer elements 508 and circuits 502 are substantially parallel with each other, and the apertures 506 are substantially axial with each other. Each branch 516*a-c* may include any number of circuits 502. Larger or smaller connectors 514 may be used to accommodate larger or smaller numbers of adjacent circuits 502.

Referring to FIG. 6, an embodiment of an energy transfer mapping device according to the present disclosure is illustrated, which includes a flexible circuit 602 spiraled into cylindrical formation of layered circuits with sensors. The circuits 602 may include any number of sensors disposed along the layers. A connector 614 at an outer end of the circuits 602 may interface with a console. The connecter 614 allows for electrical communication between the sensors and is configured to interface with a console that may include a data collection unit and display. One or more layers of test specimen of biological tissue 612 (or other material, e.g., a water-based gel) may be disposed between the layers of circuits 602. A lumen 606 is created near the center of the spiral. A plurality of inner sensors on layers of circuits 602 closer to the lumen 606 may measure energy transfer properties of simulated tissue directly exposed to energy (e.g., from cryogen fluids) in the lumen 606, similar to the surface or near surface tissue in a body lumen. A plurality of outer sensors on layers of the circuits 602 radially farther from the lumen 606 may measure energy transfer properties of simulated tissue that is farther away from the lumen, where it is not directly exposed to any energy (e.g., from cryogen fluids) in the lumen 606.

Figure 7A:
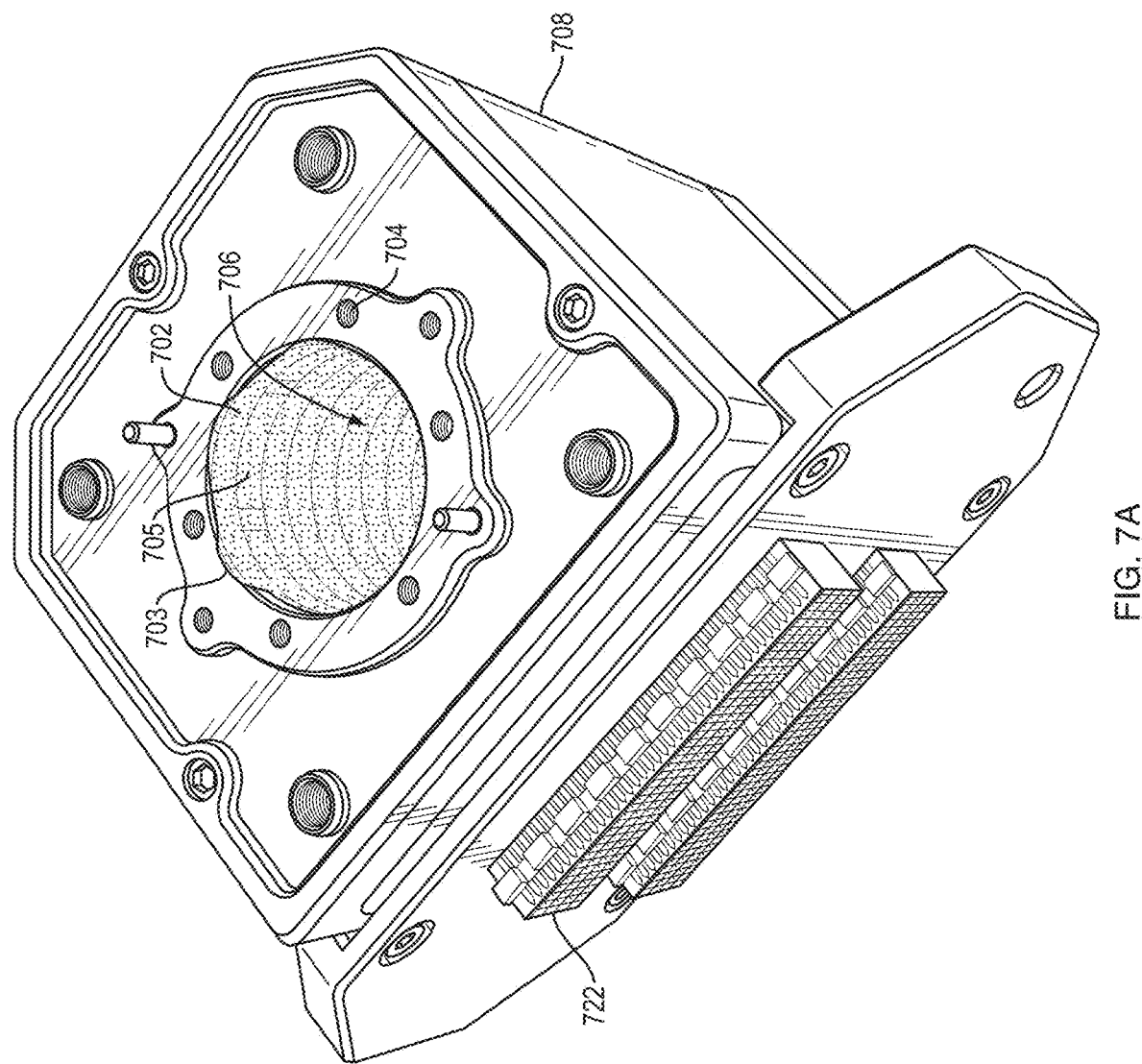
FIG. 7A illustrates a fixture housing for layered flexible circuits with sensor arrays, in accordance with an embodiment of the present disclosure.
Figure 7B:
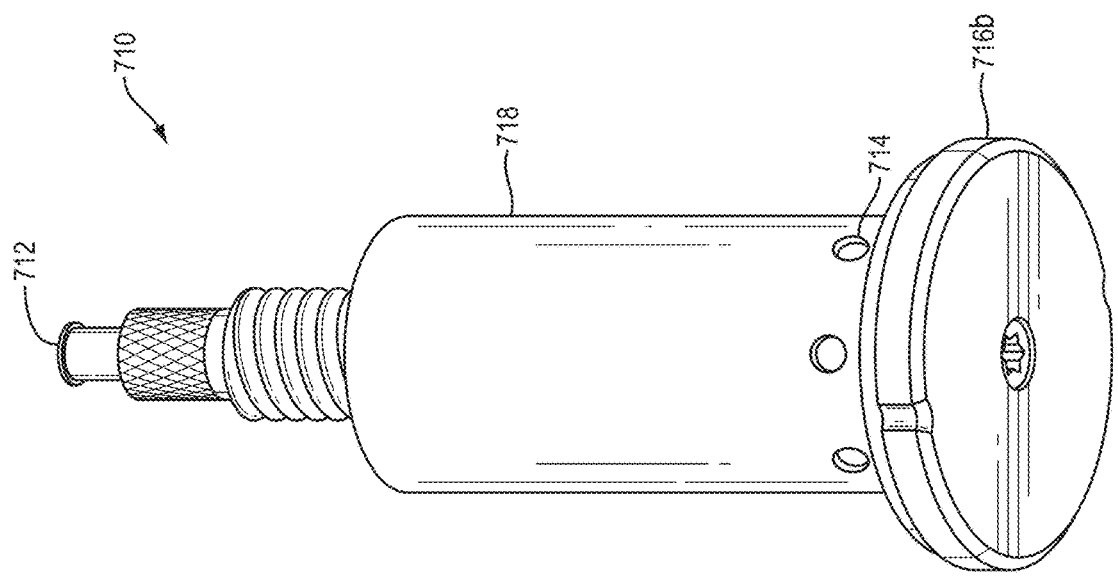
FIG. 7B illustrates an injector element for the fixture housing of FIG. 7A, in accordance with an embodiment of the present disclosure.
Figure 7C:
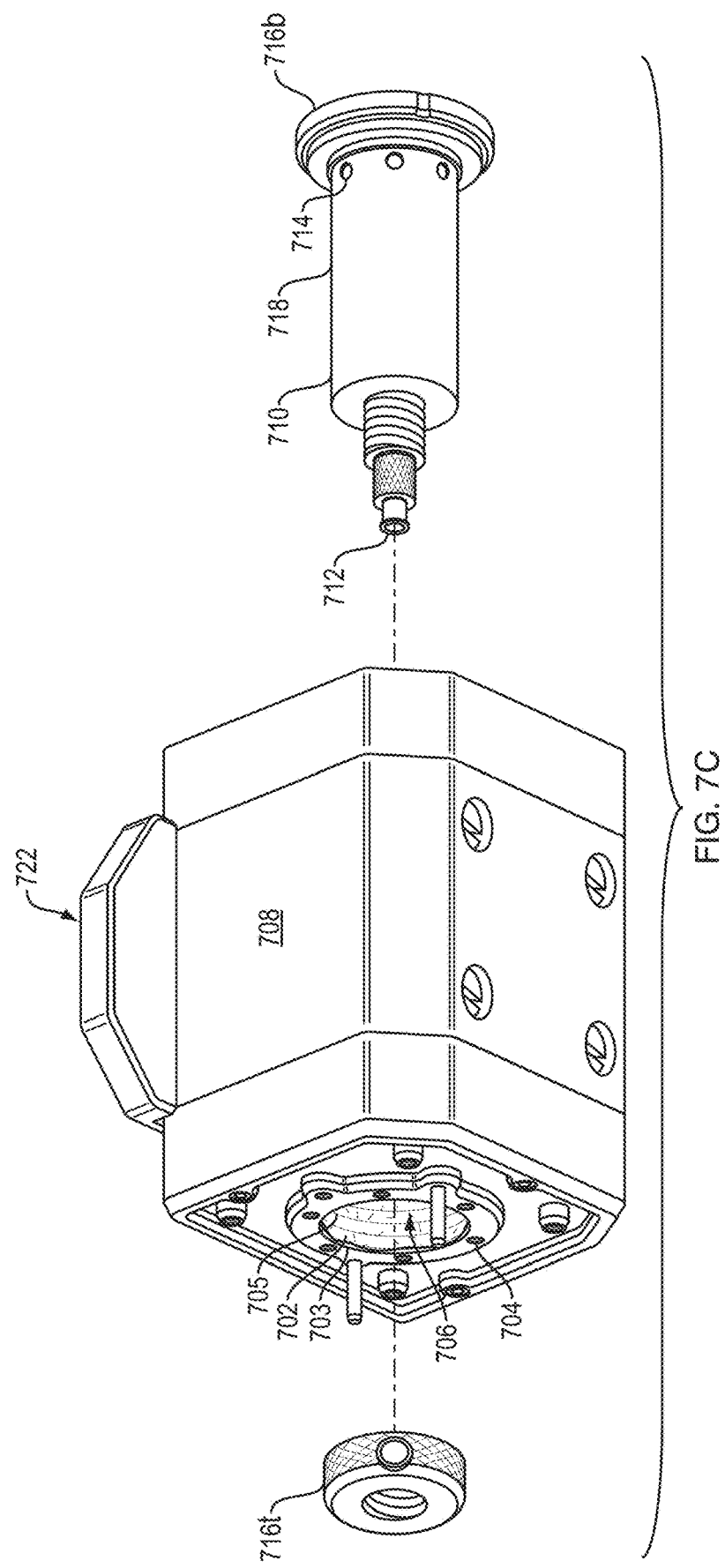
FIG. 7C illustrates the injector element of FIG. 7B disposed within the housing of FIG. 7A, in accordance with an embodiment of the present disclosure.

Referring to FIGS. 7A-7C, an embodiment of an energy transfer mapping device according to the present disclosure is illustrated, which includes a housing 708 with apertures 703 at a top of the housing and at a bottom of the housing. At least one sensor connector 722 is in electrical communication with the plurality of flexible circuits with sensor arrays 702 that are layered substantially parallel to each other along a longitudinal axis extending a length of the housing 708, with the planes of the circuits normal to the axis. The connecter 722 allows for electrical communication between the sensor arrays 702 and is configured to interface with a console that may include a data collection unit and display. Each array 702 has a plurality of sensors arranged about an edge defining an aperture extending through the array. Each sensor array 702 has one or more sensors adjacent to an aperture. The apertures of each sensor array 702 of the layered flexible circuits are substantially aligned to define a lumen 706 therethrough along a longitudinal axis of the housing. The lumen 706 is substantially aligned axially with the top and bottom apertures 706. A gel 705 may be disposed about the sensors of the sensor arrays 702. The gel 705 may be injected into the housing 708 through an injector element 710. The injector element 710 may be slidingly received within the lumen 706 and the top and bottom aperture 703 of the housing 708. The injector element 710 is receivable within the housing 708 leading with the first end through the bottom aperture 703 of the housing 708. An injector element top 716*t* may be attached (e.g., screwed) on top of the injector element 710 to prevent it from sliding out of the housing 708. The injector element 710 has a connection point 712 at a first end. The connection point 712 may be connected with a gel supply to receive the gel 705. Materials other than gels, as mentioned above, may be utilized with housing. The injector element includes at least one outlet 714 at a second end. A lumen within a body of the injector element 710 is in fluid communication with the connection point 712 and the at least one outlet 714. The gel 705 may be supplied to the connection point 712, where it flows into the lumen and out of the outlets 714. The body of the injector element 710 has an outer diameter surface 718 that may be substantially equal to a diameter of the aperture of each sensor array creating the lumen 706, and the apertures 703 of the housing 708. The bottom 716*b* of the injector element may include a back stop at the second end, further away from the first end than the at least one outlet 714, and extending radially from the longitudinal axis. The back stop at the bottom 716*b* prevents the injector element 710 from translating further within the housing 708 past the bottom aperture 703 and prevents the gel 705 from being expelled out of the housing 708 while the gel is being supplied. Vent apertures 704 in the housing 708 are substantially aligned with vents about the sensor arrays 702 through the flexible circuits. When the injector element 710 is supplied with gel 705, the gel exits the injector element 710 via the outlets 714 and into the lumen 706. The gel 705 advances from the outlets 714, through the lumen 706, towards the vent apertures 704, and exits the vent apertures 704. In this manner, the gel 705 is disposed about and covers the sensors of the sensor arrays 702. Once the gel 705 cures, the injector element 710 may be removed from the housing 708, leaving the gel 705 with a firmness sufficient to define the lumen 706 that is substantially co-axial with the apertures of each flexible circuit.

Figure 8A:
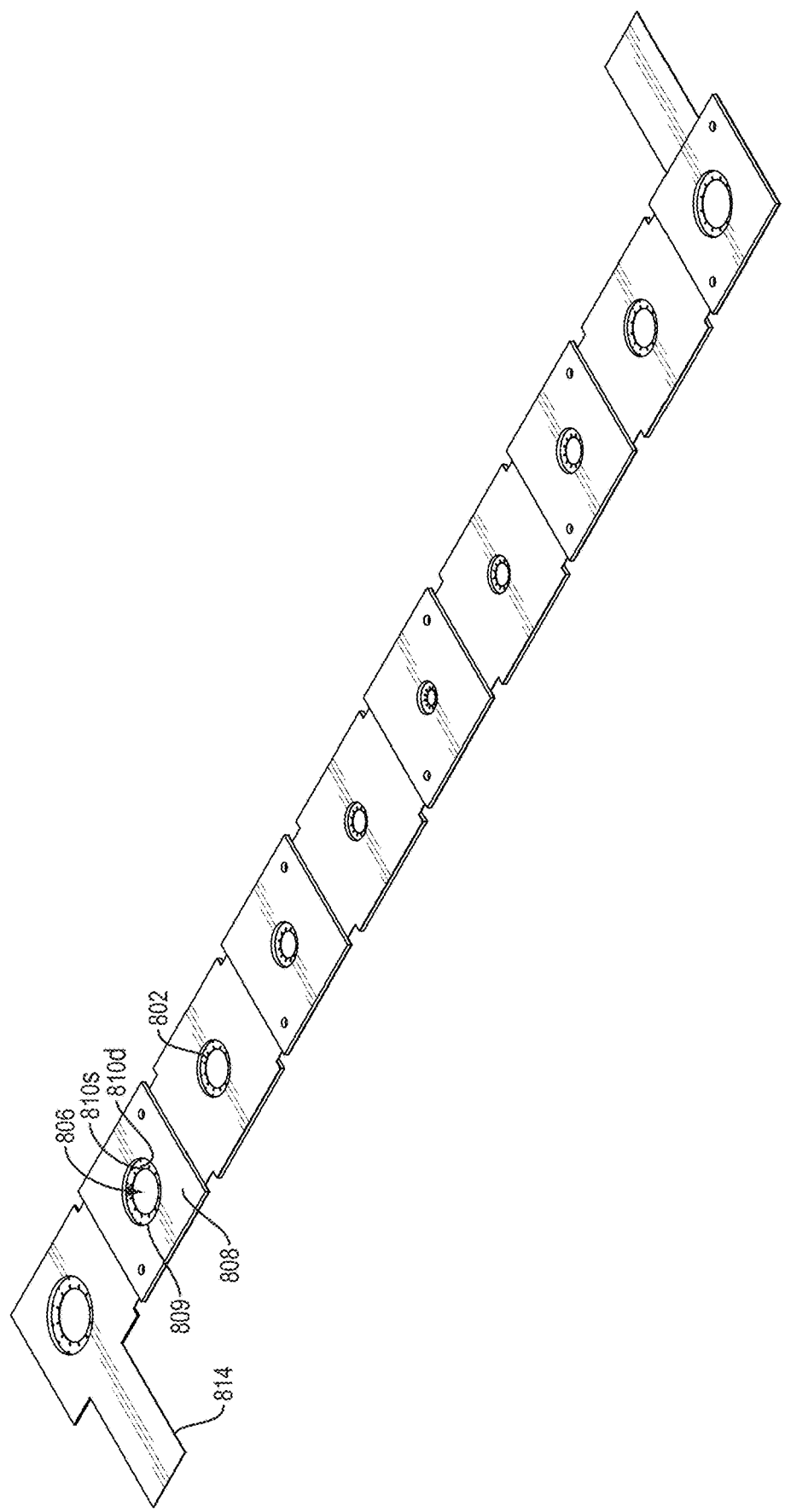
FIG. 8A illustrates an arrangement of connected flexible circuits with sensor arrays, with varying diameter apertures, in accordance with an embodiment of the present disclosure.
Figure 8B:
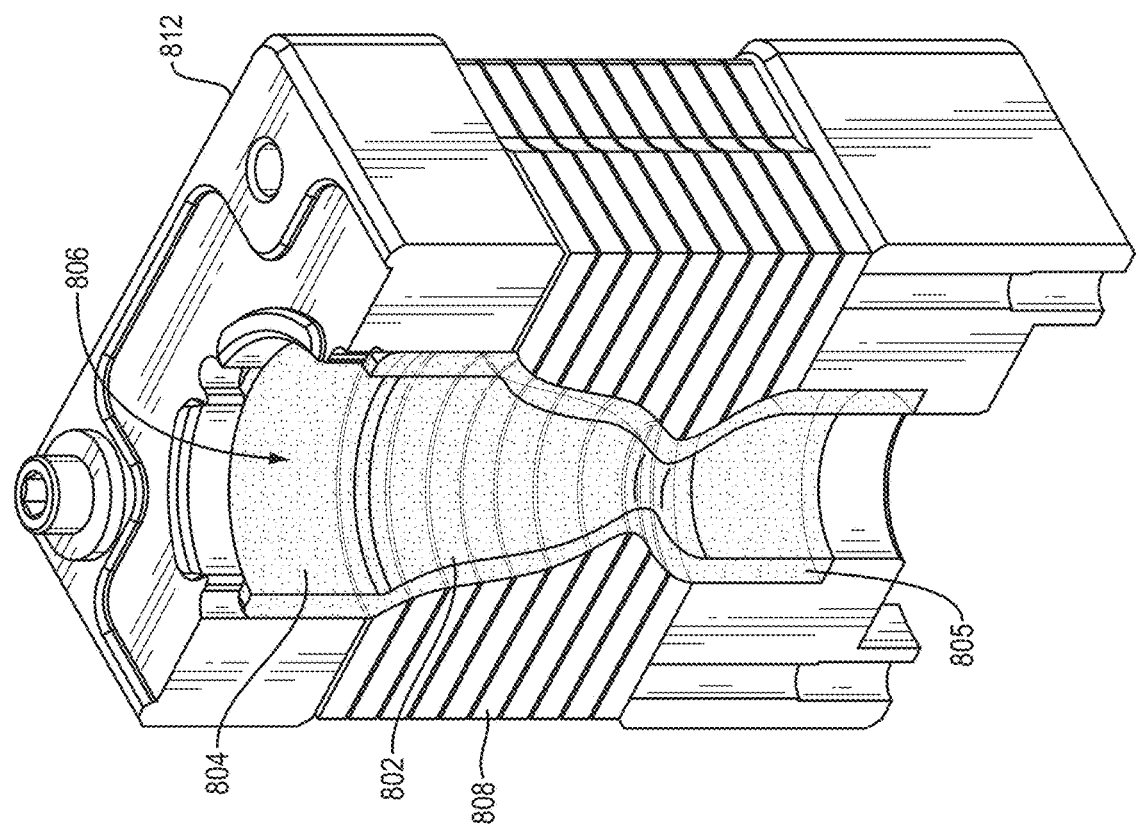
FIG. 8B illustrates a cutaway view of the arrangement of flexible circuits of FIG. 8A layered to create a fixture with a varying diameter through-lumen, in accordance with an embodiment of the present disclosure.

Referring to FIGS. 8A and 8B, an embodiment of an energy transfer mapping device according to the present disclosure is illustrated, which includes multiple flexible circuits 802. Each flexible circuit 802 includes an aperture 806 defined by an edge of the flexible circuit. A sensor array 810 includes an array of a plurality of inner sensors 810*s* and a plurality of outer sensors 810*d* arranged about the edge defining each aperture 806. A connector 814 (e.g., a ZIF connector) allows the multiple flexible circuits 802 to connect to a console or digitizer board. The setup allows the connector 814 to electrically communicate with all of the sensor arrays 810 and is configured to interface with a console that may include a data collection unit and display. The apertures 806 may vary in diameter among the flexible circuits 802. The flexible circuits 802 can be folded and layered to align each aperture 806 into a lumen 804, with a number of sensors 810*s* and 810*d* (e.g., 360 thermocouples) lining the lumen throughout the device for mapping energy transferred to and/or from an instrument inserted through the lumen. FIG. 8B illustrates the flexible circuits 802 of FIG. 8A layered together, creating the lumen 804. The lumen 804 varies in diameter along its longitudinal axis because the diameter of the apertures 806 vary between the flexible circuits 802. For example, the flexible circuits 802 of FIG. 8A may be folded and layered such that the apertures 806 create the variable diameter lumen 804 of FIG. 8B. This configuration is cast into a gel 805 acting as a tissue proxy to create a simulated narrowed trachea mold patterned from CT-scanned anatomy exhibiting tracheal stenosis. The gel 805 may be, for example, a 2-mm thick wall. In a like manner, the diameter of the apertures of layered flexible circuits may be patterned from CT-scanned (or other imaged) anatomy to simulate other body lumens.

Referring again to FIG. 8B, spacer elements 808 are disposed on the flexible circuits 802. The spacer elements

808 may be rigid laser-cut stiffeners. The spacer elements 808 may be used to space, flatten, and/or stiffen the flexible circuits 802. The spacer elements 808 may also serve to keep the apertures 806 parallel to each other. Each spacer element 808 has a spacer element aperture 809 axially aligned with the aperture 806 of the flexible circuits 802, wherein a diameter of the spacer element aperture 809 is larger than a diameter of the aperture 806 of the flexible circuits 802. End caps 812 at each end of the lumen 804 may compress the flexible circuits 802 to hold them together. Each flexible circuit 802 may have at least one vent aperture parallel to the aperture 806 of the flexible circuit 802 and between the aperture 806 and the spacer element aperture 809 of the spacer element 808.

An embodiment of an energy transfer mapping device according to the present disclosure may include a lumen (such as the configuration of the lumen 804 of FIG. 8B) created via additive manufacturing rather than via sensor arrays on multiple, layered flexible circuits. Through this manufacturing process, a three-dimensional circuit may be efficiently modeled to include any desired number of sensors and any desired size, shape, and length of a lumen. The three-dimensional circuit may then be a singular structure without discontinuities rather than with layers of one or more flexible circuits. The circuit may have a continuous circuit pathway that extends in a first dimension, a second dimension, and a third dimension rather than layering multiple circuits having multiple circuit pathways. The edge of the circuit may be continuous and may extend in the first dimension, the second dimension, and the third dimension, such as to create a varied surface and/or lumen. Additive manufacturing of embodiments of the present disclosure may include multiple materials that may be conductive and/or insulating materials (e.g., gold, copper, silver, aluminum, glass, polymerics, ceramics, and/or different combinations thereof).

Figure 9:
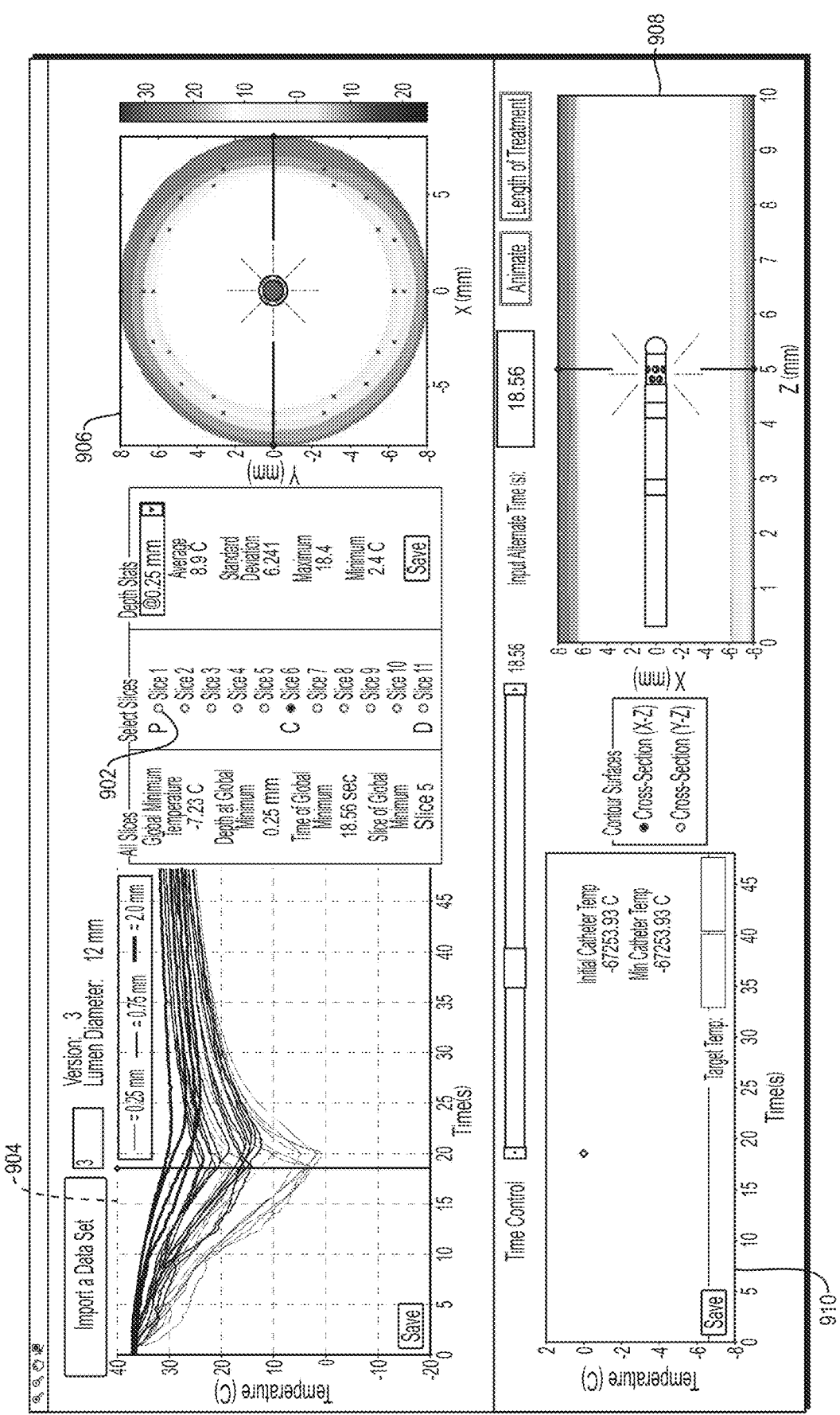
FIG. 9 illustrates an exemplary display readout for a three-dimensional energy transfer map, in accordance with an embodiment of the present disclosure.

Referring to FIG. 9, an embodiment of an energy transfer mapping device according to the present disclosure is illustrated, which includes a data collection unit and display to produce and display readable data measurements. These data measurements may directly correspond to values measured by the sensor arrays (e.g., temperature), or they may be calculated values. The measurements may be captured over time and correspond to a certain position along a lumen or aperture and at a certain depth away from an edge of a flexible circuit that defines the aperture or the lumen. For example, a sensor array of one flexible circuit may be referred to as a slice that alone displays a two-dimensional data array. However, with multiple data points from additional slices along the lumen, a three-dimensional profile may be created. An inner plurality of sensors disposed on one slice may be closer to the axial center of a lumen while an outer plurality of sensors on the same slice may be disposed farther from the axial center of the lumen. In this way, a depth profile can be measured for a slice and consolidated with other slices to create an energy transfer map along the lumen. All of these data points may be recorded, manipulated and analyzed over a procedure time and with respect to a particular instrument in order to create a range of treatment protocol for that instrument that provides an acceptable energy transfer profile when used in a body lumen and with biological tissue that corresponds to the simulated test environment. These data points may be entered into a finite element analysis matrix or multiphysics model (e.g. ANSYS® software or the like) that may use the data to illustrate, model, recreate, and/or predict parameters of the data. For example, data may be used to estimate an immeasurable property (e.g., heat flux at the surface of a gel in the lumen), which may be used to estimate a parameter value at a point where a sensor may not be located or able to be located. Analyzing data from the one or more sensor arrays may be performed on a console that includes a data collection unit and a display such as shown in FIG. 9. For example, via the console, a user may select a slice 902, which is a two-dimensional sensor array. A temperature reading over time for the sensors of the sensor array of the selected slice at various depths may be plotted 904. A three-dimensional mapping of one or more slices of sensor arrays may be illustrated in the X-Y plane 906 and the X-Z plane 908. In these planes, a certain point in time for which the data was collected may be selected and the position and temperature of the sensors of the sensor array of the slice(s) are displayed. A temperature of a medical instrument, such as a catheter, that is applying the energy to the sensor arrays may be analyzed 910 over time. Such analysis may be visualized in a time lapse video, illustrating the effects of the medical instrument on its surroundings.

In an embodiment according to the present disclosure, a mapping method includes creating a map with an instrument design in a test fixture having a three-dimensional sensor array. The fixture includes a simulated lumen configuration and a material that approximates the body lumen and tissue of the patients. The simulated lumen configuration may be defined by the plurality of edges within a plurality of layered flexible circuits. The method includes establishing a range of treatment protocol for the instrument design based on the map. The method includes instructing the treatment of the region of tissue of the patients, within the range of the treatment protocol, using an instrument comprising the instrument design. The sensor array may include at least one inner sensor at a first depth away from an edge defining a circumference of the simulated lumen and at least one outer sensor at a second depth further away from the edge than the first depth. The test fixture may comprise a plurality of flexible circuits. Each flexible circuit may include at least one inner and outer sensor. The circuits may be layered in planes extending along and normal to a longitudinal axis of the test fixture. The simulated lumen configuration may be defined by the plurality of edges aligned within a plurality of layered flexible circuits. Creating the map may include measuring an amount of energy transfer for the treatment protocol and calculating a total of the amount of energy transfer over a selected time of a treatment.

Various instruments (e.g., medical instruments) and fluids may be used or tested with the sensor arrays of the flexible circuits for measuring an energy transfer profile of the instruments. For example, a cryospray catheter with an open distal tip and/or with radial apertures at a distal end may be inserted into a lumen created by apertures of flexible circuits with sensor arrays arranged in a test fixture. The catheter may release cryogen through the tip or radial apertures of the catheter. The cryogen warms and boils as it exits the cryogen delivery catheter, resulting in a cryogen gas spray emerging from the catheter around and/or onto a gel that is surrounding the circumference of the lumen and in which the sensor arrays and flexible circuits are embedded. Such fixtures may be used to measure and display readings from the sensors within the gel as they are exposed to the energy from the cryospray to create an energy transfer map for the particular instrument. The map be configured so that it demonstrates the depth and pattern of penetration of energy transferred to and/or from the gel, thus simulating the effect that the same instrument delivering cryospray under the same conditions would have on tissue treated in the body of a patient.

All of the devices and/or methods disclosed and claimed herein can be made and executed without undue experimentation in light of the present disclosure. While the devices and methods of this disclosure have been described in terms of certain embodiments, it may be apparent to those of skill in the art that variations can be applied to the devices and/or methods and in the steps or in the sequence of steps of the methods described herein without departing from the concept, spirit and scope of the disclosure. All such similar substitutes and modifications apparent to those skilled in the art are deemed to be within the present disclosure.

What is claimed is:

1. A mapping device, comprising:
    a first flexible circuit;
    a plurality of first sensors arranged about an edge of the first flexible circuit; and
    a second flexible circuit layered in a plane substantially parallel to a plane of the first flexible circuit, the first circuit and second circuit arranged along a longitudinal axis extending a length of the device with the planes of the circuits normal to the axis; and
    the second flexible circuit having a plurality of second sensors arranged about an edge of the second flexible circuit.

2. The device of claim 1, wherein the plurality of second sensors are aligned along the longitudinal axis with the plurality of first sensors.

3. The device of claim 2, further comprising a gel in contact with the edge of the first flexible circuit and in contact with the edge of the second flexible circuit.

4. The device of claim 1, wherein the first flexible circuit is connected to the second flexible circuit; and
    wherein the second flexible circuit is foldable over the first flexible circuit where the second flexible circuit is connected to the first flexible circuit.

5. The device of claim 1, further comprising one or more spacer elements disposed between the first flexible circuit and the second flexible circuit.

6. The device of claim 1, further comprising a test specimen of biological tissue between the first flexible circuit and the second flexible circuit.

7. The device of claim 1, wherein the edges of the first circuit and the second circuit have a circumference that defines a substantially circular aperture, the aperture of each circuit having a diameter and being aligned along the longitudinal axis to form a lumen through the circuits.

8. The device of claim 7, wherein the diameter of the aperture of the first flexible circuit is different than the diameter of the aperture of the second flexible circuit.

9. The device of claim 7, further comprising a housing surrounding the first flexible circuit and the second flexible circuit, the housing having a top aperture and a bottom aperture and wherein the lumen is substantially aligned axially with the top aperture and with the bottom aperture.

10. The device of claim 9, further comprising an injector element slidingly receivable within the lumen and the top and bottom aperture of the housing, the injector element having a body and comprising:
    a connection point at a first end of the injector element to receive a gel;
    one or more outlets at a second end of the injector element to allow for the gel to exit the injector element;
    an injector lumen within the body of the injector element and in fluid communication with the connection point and the outlets; and
    wherein the body has an outer diameter substantially equal to an inner diameter of the lumen extending through the circuits.

11. The device of claim 10, wherein the injector element is receivable within the housing leading with the first end through the bottom aperture of the housing, and wherein the injector element further comprises a back stop at the second end that is further away from the first end than the outlets, the back stop configured to prevent the second end of the injector element from translating through the bottom aperture.

12. The device of claim 10, further comprising a plug-in connector in electrical communication with the plurality of first sensors and second sensors, the plug-in connector extending out of the housing and configured to interface with a console.

13. A mapping system, comprising:
    a housing including an aperture at each end of the housing;
    a plurality of sensor arrays layered in planes substantially parallel to each other within the housing along a longitudinal axis extending a length of the housing, with the planes of the arrays normal to the axis, and each array having a plurality of sensors arranged about an aperture extending through the array; and
    a gel disposed about the sensors, wherein the gel defines a lumen therethrough that is substantially aligned with the aperture of each sensor array along the longitudinal axis.

14. The system of claim 13, further comprising an injector element slidingly receivable within the lumen and the top and bottom aperture of the housing, the injector element having a body and comprising:
    a connection point at a first end of the injector element to receive a gel;
    one or more outlets at a second end of the infector element to allow for the gel to exit the injector element;
    an injector lumen within the body of the injector element and in fluid communication with the connection point and the outlets; and
    wherein the body has an outer diameter substantially equal to a diameter of the lumen extending through the circuits.

15. The system of claim 14, wherein the injector element is receivable within the housing leading with the first end through the bottom aperture of the housing, and wherein the injector element further comprises a back stop at the second end that is further away from the first end than the outlets, the back stop configured to prevent the second end of the injector element from translating through the bottom aperture.

16. The system of claim 13, further comprising at least one vent aperture in the housing to allow for the gel to exit the housing.

17. The system of claim 13, further comprising at least one sensor connector in communication with the plurality of sensor arrays and extending out of the housing.

* * * * *